US009880100B2

(12) United States Patent
Sugimoto et al.

(10) Patent No.: US 9,880,100 B2
(45) Date of Patent: Jan. 30, 2018

(54) ELECTRONIC FIELD ENHANCEMENT ELEMENT, ANALYSIS DEVICE, AND ELECTRONIC APPARATUS

(71) Applicant: Seiko Epson Corporation, Tokyo (JP)

(72) Inventors: Mamoru Sugimoto, Chino (JP); Megumi Enari, Suwa (JP); Tetsuo Mano, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/488,054

(22) Filed: Apr. 14, 2017

(65) Prior Publication Data

US 2017/0219493 A1    Aug. 3, 2017

Related U.S. Application Data

(63) Continuation of application No. 14/706,394, filed on May 7, 2015, now Pat. No. 9,658,165.

(30) Foreign Application Priority Data

May 8, 2014 (JP) .................... 2014-096554

(51) Int. Cl.
*G01J 3/44* (2006.01)
*G01N 21/65* (2006.01)
*G01N 33/483* (2006.01)

(52) U.S. Cl.
CPC ......... *G01N 21/658* (2013.01); *G01N 33/483* (2013.01)

(58) Field of Classification Search
CPC ................ G01N 21/65; G01N 21/658; G01N 2021/656; G01J 3/44; G01J 3/02

USPC ......................................................... 356/301
See application file for complete search history.

(56) References Cited

U.S. PATENT DOCUMENTS

| | | | |
|---|---|---|---|
| 3,979,184 | A | 9/1976 | Giaever |
| 7,351,588 | B2 | 4/2008 | Poponin |
| 7,639,355 | B2 | 12/2009 | Fattal et al. |
| 7,643,156 | B2 | 1/2010 | Naya et al. |
| 7,705,989 | B2 | 4/2010 | Chaton et al. |
| 7,999,934 | B2 | 8/2011 | Naya et al. |

(Continued)

FOREIGN PATENT DOCUMENTS

| | | |
|---|---|---|
| EP | 2372348 A1 | 10/2011 |
| JP | 61-37581 | 8/1986 |

(Continued)

OTHER PUBLICATIONS

Jean Cesario, "Electromagnetic Coupling Between a Metal Nanoparticle Grating and a Metallic Surface", Optic Letters, vol. 30 No. 24, pp. 3404-3406, Dec. 15, 2005.

(Continued)

*Primary Examiner* — Tarifur Chowdhury
*Assistant Examiner* — M D M Rahman
(74) *Attorney, Agent, or Firm* — Harness, Dickey & Pierce, P.L.C.

(57) ABSTRACT

An electronic field enhancement element includes: a metal layer; a dielectric layer provided on the metal layer; and a plurality of fine metal structures provided on the dielectric layer. A refractive index n of the dielectric layer satisfies $n'=n+i\kappa$ and is in a range of $1 \leq n < 1.46$, wherein a complex refractive index of the dielectric layer is $n'$, an imaginary unit is $i$, and an extinction coefficient is $\kappa$.

14 Claims, 15 Drawing Sheets

(56) References Cited

U.S. PATENT DOCUMENTS

| | | | |
|---|---|---|---|
| 8,023,114 B2 | 9/2011 | Yamamichi et al. | |
| 8,314,935 B2 | 11/2012 | Handa et al. | |
| 8,441,631 B2 | 5/2013 | Wang et al. | |
| 8,817,263 B2 | 8/2014 | Sugimoto et al. | |
| 8,836,946 B2 | 9/2014 | Amako et al. | |
| 8,836,947 B2 | 9/2014 | Amako et al. | |
| 8,867,032 B2 | 10/2014 | Van Dorpe et al. | |
| 8,877,519 B2 | 11/2014 | Yamada et al. | |
| 2005/0068883 A1* | 3/2005 | Kondo | G11B 7/24038 369/288 |
| 2007/0178315 A1 | 8/2007 | Thomas et al. | |
| 2010/0233825 A1* | 9/2010 | Yamada | G01N 21/554 436/525 |
| 2012/0081703 A1 | 4/2012 | Moskovits et al. | |
| 2013/0057857 A1 | 3/2013 | Jamshidi et al. | |
| 2013/0092823 A1 | 4/2013 | Amako et al. | |
| 2013/0176562 A1 | 7/2013 | Shioi et al. | |

FOREIGN PATENT DOCUMENTS

| | | |
|---|---|---|
| JP | 2007-024870 A | 2/2007 |
| JP | 2008-014933 A | 1/2008 |
| JP | 04156567 B2 | 9/2008 |
| JP | 2009-085724 A | 4/2009 |
| JP | 2009-115492 A | 5/2009 |
| JP | 2010-531995 A | 9/2010 |
| JP | 4806411 B2 | 11/2011 |
| JP | 4878238 B2 | 2/2012 |
| JP | 2012-132804 A | 7/2012 |
| JP | 5000300 B2 | 8/2012 |
| JP | 2013-007614 A | 1/2013 |
| JP | 2013-088223 A | 5/2013 |
| JP | 2013-142546 A | 7/2013 |
| JP | 2013-148420 A | 8/2013 |
| JP | 2013-148421 A | 8/2013 |
| JP | 2013-221883 A | 10/2013 |
| WO | WO-2005-033335 A2 | 4/2005 |
| WO | WO-2005-114298 A2 | 12/2005 |
| WO | WO-2009-002524 A2 | 12/2008 |
| WO | WO-2012-011998 A2 | 1/2012 |

OTHER PUBLICATIONS

Wen-Di Li, Fei Ding, Three-Dimensional Cavity Nanoantenna Coupled Plasmonic Nanodots for Ultrahigh and Uniform Surface-Enhanced Raman Scattering Over Large are, Feb. 13, 2011, vol. 19, pp. 3925-3936.

* cited by examiner

| INDEX n | X180Y600_AG ||| X140Y400_AU |||
| --- | --- | --- | --- | --- | --- | --- |
| | SQRT at 655nm | DIAMETER | GAP THICKNESS | SQRT at 655nm | DIAMETER | GAP THICKNESS |
| 1 | 87 | 126 | 120 | | | |
| 1.46 | 135 | 104 | 30 | 104 | 86 | 50 |
| 1.64 | | | | 122 | 76 | 40 |
| 1.77 | 183 | 84 | 40 | | | |
| 2.16 | 210 | 58 | 30 | 169 | 48 | 50 |
| 2.3 | 208 | 50 | 30 | | | |
| 2.4 | 196 | 44 | 30 | | | |
| 2.49 | 152 | 40 | 30 | 133 | 28 | 40 |

FIG.17

ELECTRONIC FIELD ENHANCEMENT ELEMENT, ANALYSIS DEVICE, AND ELECTRONIC APPARATUS

CROSS-REFERENCE TO RELATED APPLICATIONS

This is a continuation patent application of U.S. application Ser. No. 14/706,394 filed May 7, 2015, which claims priority to Japanese Patent Application No. 2014-096554 filed May 8, 2014, all of which are expressly incorporated herein by reference in their entireties.

BACKGROUND

1. Technical Field

The present invention relates to an electronic field enhancement element, an analysis device, and an electronic apparatus.

2. Related Art

In various medical and health fields and in areas relating to environment, food, and public security, a sensing technology for rapidly and easily detecting trace substances with high sensitivity and high accuracy is required. The trace substances which are a target to be detected are very diverse and biologically-relevant substances such as bacteria, viruses, proteins, nucleic acids, and various antigens and antibodies or various compounds containing inorganic molecules, organic molecules, and polymers. In the related art, the detection of these trace substances was performed through sampling, analysis, and interpretation, but a dedicated device and a skillful inspection operator were necessary, and accordingly, it was difficult to perform the analysis without delay. Therefore, a long period of time (more than several days) is required to obtain results from an inspection. Thus, a sensing technology is strongly required to be rapid and simple, and development of a sensor which can respond to the requests is required. For example, a diagnosis of a patient in an airport showing signs of fever, along with diarrhea and emesis (vomiting) is an urgent issue, in order to prevent the spread of infectious diseases. In the infectious disease testing, different treatments are performed depending on the cause of the disease such as being bacterial or viral, and it is important to rapidly identify the type of bacteria or virus, in order to stop the spread of infection.

With such requests, in recent years, various types of sensors using an electrochemical method have been investigated, and an interest in a sensor using surface plasmon resonance (SPR) has increased due to integration ability, low cost, and a high degree of freedom of the measurement environment. For example, a sensor which detects adsorption of the substance such as adsorption of antigens in an antigen-antibody reaction using the SPR generated on a metal thin film provided on a surface of a total reflective prism, has been known. A method of detecting Raman scattering of the substance attached to a sensor portion using surface enhanced Raman scattering (SERS) and identifying the attached substance has also been investigated.

As a structure of such as sensor, OPTICS LETTERS, Vol. 30, No. 24, 2005, 3404-3406, for example, discloses a sensor element having a structure (Gap type Surface Plasmon Polariton (GSPP) structure) in which a $SiO_2$ thin film is formed on a gold thin film and a gold disk is formed thereon.

The element disclosed in OPTICS LETTERS, Vol. 30, No. 24, 2005, 3404-3406 employs a $SiO_2$ layer as a dielectric body disposed between a metal layer and a metal particle. However, according to the investigation of the inventors, it has been found that a refractive index of a dielectric layer strongly affects a degree of electronic field enhancement of the element and distribution of a hot spot.

SUMMARY

An advantage of some aspects of the invention is to provide an electronic field enhancement element, an analysis device, and an electronic apparatus having a high electronic field enhancement effect based on surface plasmon resonance.

The invention can be implemented as the following forms or application examples.

An aspect of the invention is directed to an electronic field enhancement element including: a metal layer; a dielectric layer which is provided on the metal layer; and a plurality of fine metal structures which are provided on the dielectric layer, in which a refractive index n of the dielectric layer satisfies an expression of $n'=n+i\kappa$ and is in a range of $1 \leq n < 1.46$, when a complex refractive index of the dielectric layer is set as n', an imaginary unit is set as i, and an extinction coefficient is set as κ.

According to the electronic field enhancement element, the range of the refractive index n of the dielectric layer is excellent and a high electronic field enhancement effect is obtained. Accordingly, it is possible to detect the target substance and determine the quantity thereof with high sensitivity, for example.

In the electronic field enhancement element according to the aspect of the invention, the fine metal structures may be arranged at a first pitch P1 in a first direction intersecting with a thickness direction of the dielectric layer and be arranged at a second pitch P2 in a second direction intersecting with the first direction, and the first pitch P1 and the second pitch P2 may satisfy the following expression (1).

$$P1 < P2 \leq Q + P1 \qquad (1)$$

Here, Q represents a pitch of diffraction grating applied in the following equation (2) by setting an angular frequency of localized plasmon excited in the fine metal structures as ω, a dielectric constant of the metal configuring the metal layer as $\in(\omega)$, a circumferential dielectric constant of the metal layer as $\in$, the speed of light in vacuum as c, and an irradiation angle of the incident light which is an inclined angle in the thickness direction of the metal layer as θ.

$$((\omega/c) \cdot \{\in \cdot \in(\omega)/(\in + \in(\omega))\})^{1/2} = \in^{1/2} \cdot (\omega/c) \sin \theta + 2m\pi/Q \; (m = \pm 1, \pm 2, \ldots) \qquad (2)$$

According to the electronic field enhancement element, since the range of the refractive index n of the dielectric layer is excellent and the arrangement of the fine metal structures is excellent, a higher electronic field enhancement effect is obtained. Accordingly, it is possible to detect the target substance and determine the quantity thereof with high sensitivity, for example.

In the electronic field enhancement element according to the aspect of the invention, the refractive index n of the dielectric layer may be in a range of $1.8 < n < 2.2$.

According to the electronic field enhancement element, since the range of the refractive index n of the dielectric layer is further excellent, a higher electronic field enhancement effect is obtained.

Another aspect of the invention is directed to an electronic field enhancement element including: a metal layer; a dielectric layer which is provided on the metal layer; and a plurality of fine metal structures which are arranged on the dielectric layer at a first pitch P1 in a first direction and are arranged at a second pitch P2 in a second direction intersecting with the first direction, in which the first pitch P1 and the second pitch P2 satisfy a relationship of the following expression (1):

$$P1 < P2 \leq Q + P1 \quad (1)$$

Here, Q represents a pitch of diffraction grating applied in the following equation (2) by setting an angular frequency of localized plasmon excited in the fine metal structures as ω, a dielectric constant of the metal configuring the metal layer as $\in(\omega)$, a circumferential dielectric constant of the metal layer as $\in$, the speed of light in vacuum as c, and an irradiation angle of the incident light which is an inclined angle in the thickness direction of the metal layer as θ.

$$((\omega/c) \cdot \{\in \cdot \in(\omega)/(\in + \in(\omega))\}^{1/2} = \in^{1/2} \cdot (\omega/c) \sin \theta + 2m\pi/Q \ (m = \pm 1, \pm 2, \ldots) \quad (2)),$$

and a refractive index n of the dielectric layer satisfies an expression of n'=n+iκ and is in a range of 1≤n<1.46, when a complex refractive index of the dielectric layer is set as n', an imaginary unit is set as i, and an extinction coefficient is set as κ.

According to the electronic field enhancement element, it is possible to increase energy distribution to the enhancement electronic field in a hot spot of the top end of the fine metal structure, without greatly sacrificing the electronic field enhancement effect. Accordingly, it is possible to detect the target substance and determine the quantity thereof with high sensitivity, for example.

Still another aspect of the invention is directed to an analysis device including: the electronic field enhancement element described above; a light source which irradiates the electronic field enhancement element with at least one kind of incident light among linearly polarized light in the first direction, linearly polarized light in the second direction, and circularly polarized light; a detector which detects light radiated from the electronic field enhancement element.

According to the analysis device, the analysis device can detect the target substance and determine the quantity thereof with high sensitivity, for example.

In the analysis device according to the aspect of the invention, the detector may detect Raman scattering light enhanced by the electronic field enhancement element.

Yet another aspect of the invention is directed to an electronic apparatus including: the analysis device described above; an operation unit which operates health care information based on detected information from the detector; a storage unit which stores the health care information; and a display unit which displays the health care information.

According to the electronic apparatus, the electronic field enhancement element having a great enhancement degree of light based on plasmon is obtained, and accordingly, it is possible to easily detect trace substances and to provide the health care information with high accuracy.

In the electronic apparatus according to the aspect of the invention, the health care information may include information regarding at least one of biologically-relevant substances selected from a group consisting of bacteria, viruses, proteins, nucleic acid, and antigens and antibodies or existence or non-existence or an amount of at least one kind of compound selected from inorganic molecules and organic molecules.

According to the electronic apparatus, it is possible to provide effective health care information.

BRIEF DESCRIPTION OF THE DRAWINGS

Embodiments of the invention will be described with reference to the accompanying drawings, wherein like numbers reference like elements.

FIG. 17 is a table in which results obtained by searching conditions showing a peak value of SQRT are arranged (Table 1).

DESCRIPTION OF EXEMPLARY EMBODIMENTS

Hereinafter, embodiments of the invention will be described. The embodiments hereinafter merely describe an example of the invention. The invention is not limited to the following embodiments and includes various modified embodiments executed within a range not departing from the gist of the invention. All configurations described hereinafter are not necessarily compulsory configurations of the invention.

1. ELECTRONIC FIELD ENHANCEMENT ELEMENT

Figure 1:
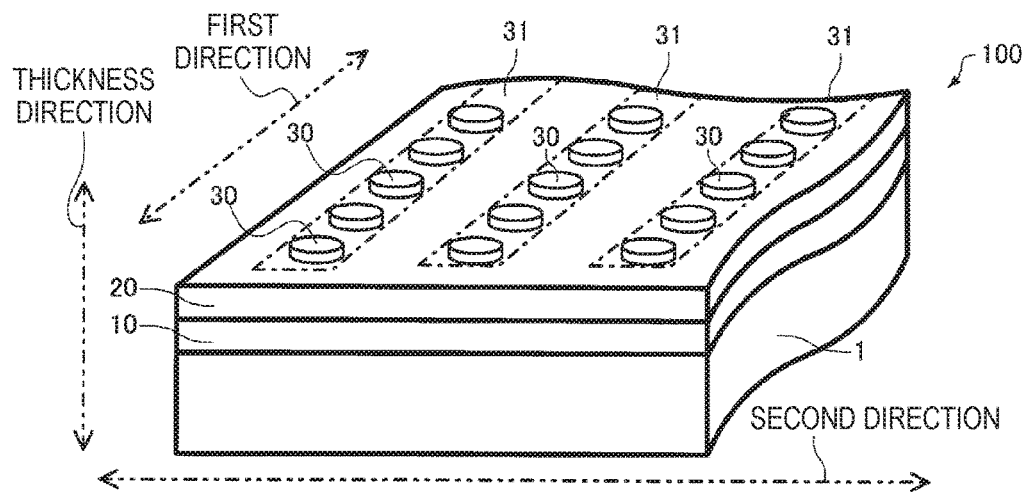
FIG. 1 is a perspective view schematically showing an electronic field enhancement element of the embodiment.
Figure 2:
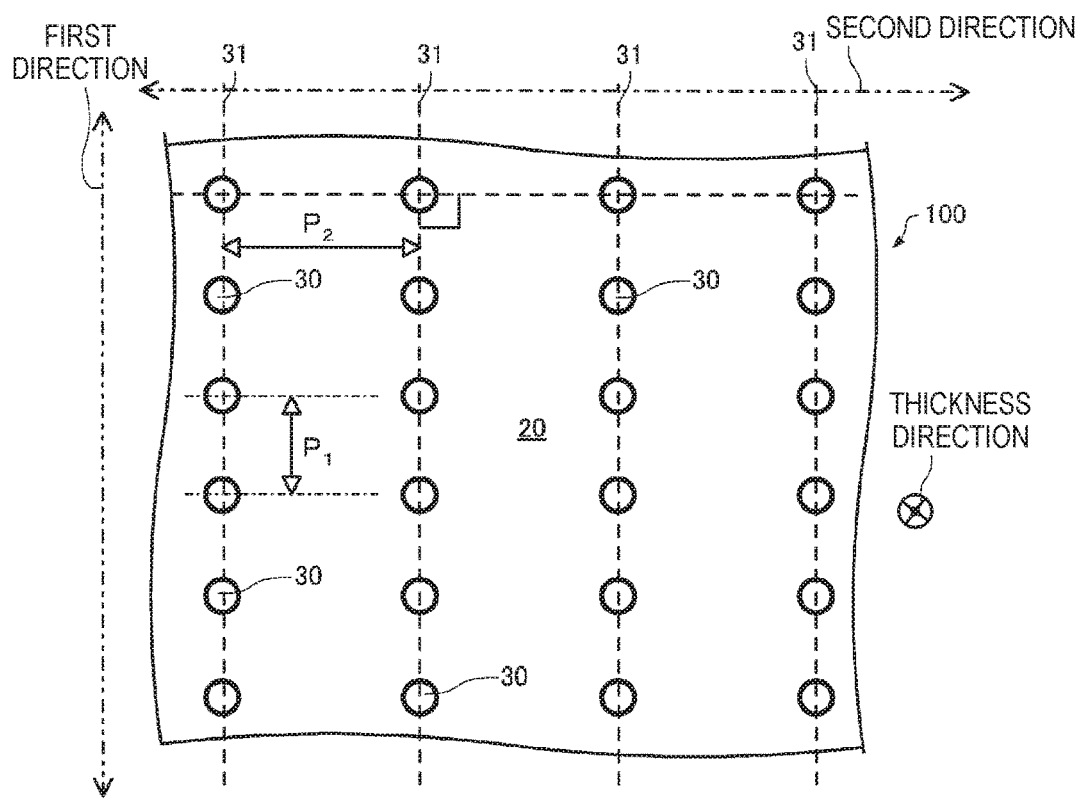
FIG. 2 is a schematic view when the electronic field enhancement element of the embodiment is seen in a thickness direction of a metal layer.
Figure 3:
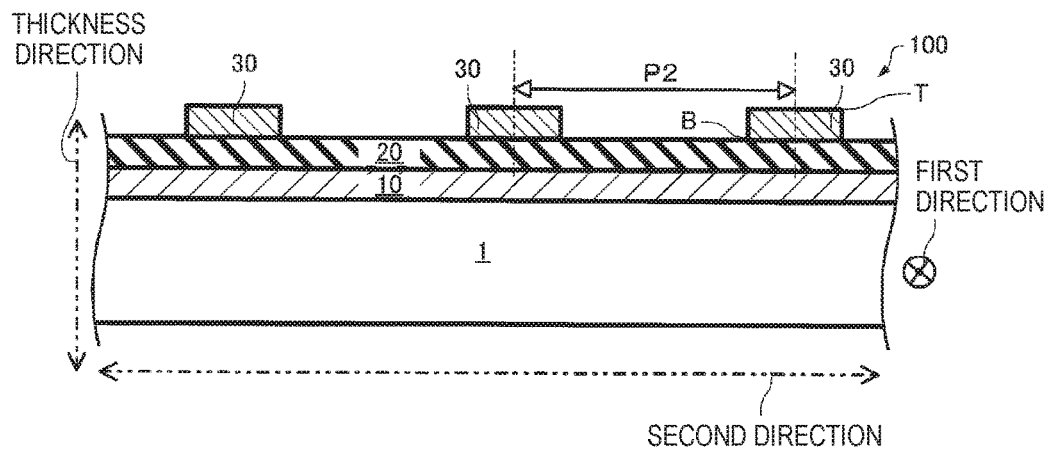
FIG. 3 is a schematic view of a cross section orthogonal to a first direction of the electronic field enhancement element of the embodiment.
Figure 4:
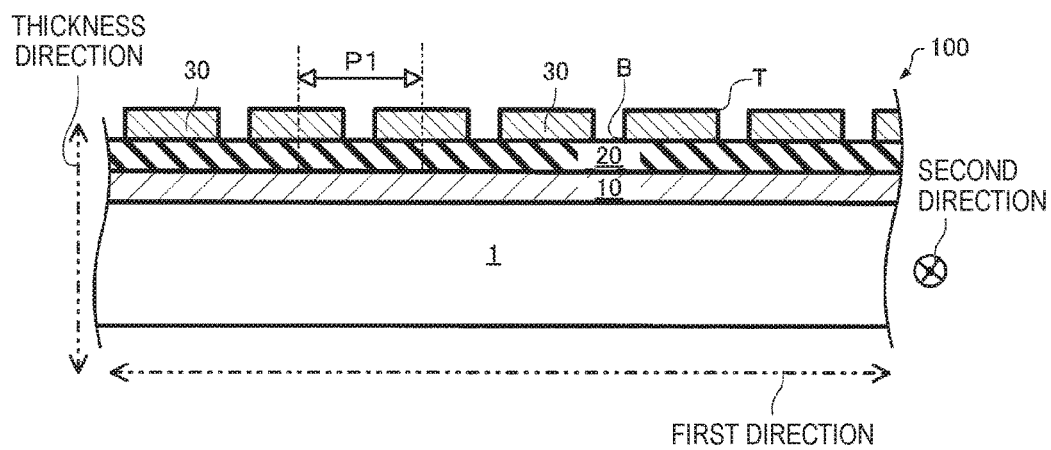
FIG. 4 is a schematic view of a cross section orthogonal to a second direction of the electronic field enhancement element of the embodiment.

FIG. 1 is a perspective view of an electronic field enhancement element 100 according to an example of the embodiment. FIG. 2 is a schematic view when the electronic field enhancement element 100 according to an example of the embodiment is seen in a plan view (in a thickness direction of a dielectric layer). FIGS. 3 and 4 are schematic views of the electronic field enhancement element 100 according to an example of the embodiment. The electronic field enhancement element 100 of the embodiment includes a metal layer 10, a dielectric layer 20, and fine metal structures 30.

1.1. Metal Layer

The shape of the metal layer 10 is not particularly limited, as long as it has a surface of metal, and the metal layer may have a thick plate shape or a shape of a film or a layer, for example. The metal layer 10 may be provided on a substrate 1, for example. The material of the substrate 1 in this case is not particularly limited, but a material which hardly affects a propagating surface plasmon excited on the metal layer 10 is preferable. Examples of the substrate 1 include a glass substrate, a silicon substrate, and a resin substrate. The shape of the surface of the substrate 1 where the metal layer 10 is provided, is also not particularly limited. In a case of forming an ordered structure on the surface of the metal layer 10, the substrate may have a surface corresponding to the ordered structure, and in a case where the surface of the metal layer 10 is flat, the substrate may have a flat surface. In examples shown in FIGS. 1 to 4, the metal layer 10 is provided on the surface (flat surface) of the substrate 1.

Herein, the expression "flat surface" does not mean a mathematically strict flat surface which is flat (smooth) without any slight unevenness. Unevenness caused by atom configuration or unevenness caused by a two-dimensional structure (crystal, grain aggregate, or grain boundary) of substance configuration may be present on the surface, and accordingly, the surface thereof may not be an exact flat surface, in the microscopic sense. However, even in this case, the unevenness is not recognized in a macroscopic sense, and the surface thereof is observed so as to be called a flat surface. Accordingly, in this specification, when the flat surface is recognized in such a macroscopic sense, this is called a flat surface.

In addition, in this specification, the expressions such as "up" and "down" are not expressions meaning a vertical relationship dependent on an installation state of the electronic field enhancement element. The above expressions mean a vertical relationship in a state where the substrate is present on the lower side (the viewing field is set so that the substrate is on the lower side), regardless of the installation state of the electronic field enhancement element. Accordingly, if the viewing field is set so that a direction of the action of the gravity heads towards the lower side, for example, the expression that the metal layer is provided over the substrate, means that the viewing field is set so that the substrate is positioned on the lower side (that is, the direction of the action of the gravity heads the upper side, in this case) and the metal layer is literally positioned over the substrate, even when the electronic field enhancement element is installed so that the substrate is on the upper side and the metal layer is on the lower side.

In the embodiment, a thickness direction of the metal layer 10 coincides with a thickness direction of the dielectric layer 20 which will be described later. In this specification, the thickness direction of the metal layer 10 or the thickness direction of the dielectric layer 20 may be called a thickness direction or a height direction when describing the fine metal structures 30 which will be described later. When the metal layer 10 is provided on the surface of the substrate 1, for example, a normal direction of the surface of the substrate 1 is called a thickness direction or a height direction.

The metal layer 10 can be, for example, formed by a method such as vapor deposition, sputtering, casting, or machining. When the metal layer 10 is provided on the substrate 1, the metal layer may be provided on the entire surface of the substrate 1 or may be provided on a part of the surface of the substrate 1. The thickness of the metal layer 10 is not particularly limited, as long as the propagating surface plasmon can be excited on the surface of the metal layer 10 or the vicinity of the boundary between the metal layer 10 and the dielectric layer 20. The thickness thereof can be, for example, from 10 nm to 1 mm, preferably from 20 nm to 100 µm, and more preferably from 30 nm to 1 µm.

The metal layer 10 is configured with metal having an electronic field in which an electronic field applied by excitation light and polarization induced by the electronic field are vibrated mutually in opposite phases, that is, metal having a negative value of a real part of a dielectric function (negative dielectric constant) and a dielectric constant of an imaginary part which is smaller than an absolute value of the dielectric constant of the real part, when a specific electronic field is applied. Examples of the metal which has such dielectric constants include gold, silver, aluminum, copper, platinum, and an alloy thereof. When using light in a visible light region as the excitation light, the metal layer 10 preferably includes a layer formed of gold, silver, or copper among the above metals. The surface of the metal layer 10 (end surface in the thickness direction) may be or may not be a specific crystal plane. The metal layer 10 may be formed with a plurality of metal layers.

The metal layer 10 has a function of generating the propagating surface plasmon (PSP) in the electronic field enhancement element 100 of the embodiment. When performing the incidence of light to the metal layer 10 in conditions which will be described later, the propagating surface plasmon is generated in the vicinity of the surface of the metal layer (end surface in the thickness direction). In this specification, a quantum of vibration obtained by coupling vibration of charges in the vicinity of the surface of the metal layer 10 and an electromagnetic wave is called a surface plasmon polariton (SPP). The propagating surface plasmon generated on the metal layer 10 can perform interaction (this may be called a "hybrid" in this specification) with the localized surface plasmon (LSP) generated on the fine metal structures 30 which will be described later under certain conditions. In addition, the metal layer 10 also has a function as a mirror reflecting light (for example, refracted light of excitation light) towards the dielectric layer 20 side.

1.2. Dielectric Layer

The electronic field enhancement element 100 of the embodiment includes the dielectric layer 20 for separating the metal layer 10 and the fine metal structures 30 from each other. FIGS. 1 to 4 show the dielectric layer 20. The dielectric layer 20 can have a shape of a film or a layer. The dielectric layer 20 is provided on the metal layer 10.

Accordingly, the metal layer 10 and the fine metal structures 30 can be separated from each other. In addition, the dielectric layer 20 can allow the excitation light to penetrate therethrough.

The dielectric layer 20 can be formed by a method such as vapor deposition, sputtering, CVD, and various coating methods. The dielectric layer 20 may be provided on the entire surface of the metal layer 10 or may be provided on a part of the surface of the metal layer 10.

The dielectric layer 20 is formed with a dielectric body. The dielectric body has a relative dielectric constant $\in$. A real part $\in'$ and an imaginary part $\in''$ of the relative dielectric constant $\in$ are respectively obtained with equations of $\in'=n^2-\kappa^2$ and $\in''=2n\kappa$. Herein, n represents a refractive index and $\kappa$ (kappa) represents an extinction coefficient.

When the refractive index of the dielectric layer 20 is set as n and the extinction coefficient thereof is set as $\kappa$, a complex refractive index n' of the dielectric layer 20 is represented as $n'=n+i\kappa$. Since the dielectric layer 20 is a so-called thin film, the extinction coefficient $\kappa$ is assumed to satisfy an expression of $0 \le \kappa < 0.02$.

Accordingly, since the extinction coefficient $\kappa$ is sufficiently small, the refractive index n of the dielectric layer 20 satisfies that $n=\in^{1/2}$.

The refractive index n of the dielectric layer 20 is preferably in a range of $1.46<n<2.5$. Although the details will be described later, the range has a high total electronic field enhancement degree of the electronic field enhancement element 100. The range having a higher electronic field enhancement degree is $1.5<n<2.4$, preferably $1.6<n<2.3$, more preferably $1.8<n<2.2$, even more preferably $2.0<n<2.2$, and particularly preferably $2.1<n<2.2$. This will be shown in the experimental example, but the total electronic field enhancement degree is highest when n is approximately 2.16. A material of the dielectric layer 20 having n of approximately 2.16, tantalum pentoxide ($Ta_2O_5$), is exemplified, and this can be preferably used. Meanwhile, when increasing the electronic field enhancement degree of the top end of the fine metal structure 30, even when the total electronic field enhancement degree is slightly low, the refractive index of the dielectric layer 20 is preferably in a range of $1 \le n < 1.46$.

The dielectric layer 20 preferably has a positive dielectric constant, and can be formed with a copolymer such as silicon oxide ($SiO_x$, for example, $SiO_2$), aluminum oxide ($Al_xO_y$, for example, $Al_2O_3$), tantalum oxide ($Ta_2O_5$), silicon nitride ($Si_3N_4$), titanium oxide ($TiO_x$, for example, $TiO_2$), or polymethylmethacrylate (PMMA), and indium tin oxide (ITO). The dielectric layer 20 may be configured with a plurality of layers having different materials from each other.

A thickness G of the dielectric layer 20 is set so that the propagating surface plasmon generated on the surface of the metal layer 10 and the localized surface plasmon of the fine metal structures 30 perform the interaction. For example, the thickness G (nm) of the dielectric layer 20 is from 5 nm to 300 nm, preferably from 10 nm to 280 nm, more preferably from 15 nm to 260 nm, even more preferably from 20 nm to 200 nm, and particularly preferably from 20 nm to 150 nm.

1.3. Fine Metal Structures

The fine metal structures 30 are provided to be separated from the metal layer 10 in the thickness direction. That is, the fine metal structures 30 are provided on the dielectric layer 20 and are disposed to be spatially separated from the metal layer 10. The dielectric layer 20 exists between the fine metal structures 30 and the metal layer 10. In the example of the electronic field enhancement element 100 shown in FIGS. 1 to 4 of the embodiment, the dielectric layer 20 is provided on the metal layer 10, and the fine metal structures 30 are provided thereon, and therefore, the metal layer 10 and the fine metal structures 30 are disposed to be separated in the thickness direction of the dielectric layer 20.

The shape of the fine metal structures 30 is not particularly limited. For example, the shape of the fine metal structures 30 can be a circle, an ellipse, a polygon, an indefinite shape or a combined shape thereof, when projected in the thickness direction of the metal layer 10 or the dielectric layer 20 (in a plan view in the thickness direction), or can be a circle, an ellipse, a polygon, an indefinite shape or a combined shape thereof, when projected in a direction orthogonal to the thickness direction. In the examples shown in FIGS. 1 to 7, all of the fine metal structures 30 are shown to have a circular shape having a central axis in the thickness direction of the dielectric layer 20, but the shape of the fine metal structures 30 is not limited thereto.

A size T of the fine metal structures 30 in the height direction indicates a length of a section obtained by cutting the fine metal structures 30 by the plane orthogonal to the height direction, and is from 1 nm to 100 nm. For example, when the shape of the fine metal structures 30 is a cylinder having the height direction as a central axis, the size of the fine metal structures 30 in the height direction (height of the cylinder) is from 1 nm to 100 nm, preferably from 2 nm to 50 nm, more preferably from 3 nm to 30 nm, and even more preferably from 4 nm to 30 nm.

A size of the fine metal structures 30 in a first direction orthogonal to the height direction indicates a length of a section obtained by cutting the fine metal structures 30 by the plane orthogonal to the first direction, and is from 5 nm to 200 nm. When the shape of the fine metal structures 30 is a cylinder having the height direction as a central axis, the size of the fine metal structures 30 in the first direction (diameter of the bottom surface of the cylinder) is from 10 nm to 200 nm, preferably from 20 nm to 180 nm, more preferably from 25 nm to 150 nm, and even more preferably from 30 nm to 72 nm.

In this specification, the size of the fine metal structures 30 in the first direction (diameter of the bottom surface of the cylinder) in a case where the shape of the fine metal structures 30 is a cylinder having the height direction as a central axis, is noted as 100 D (diameter of 100 nm), for example, with a symbol "D".

The shape and the material of the fine metal structures 30 are arbitrary as long as the localized surface plasmon can be generated by irradiation with the excitation light, but examples of the material which can generate the localized surface plasmon by the light in the vicinity of the visible light include gold, silver, aluminum, copper, platinum, and an alloy thereof.

The fine metal structures 30 can be, for example, formed by a method of performing patterning after forming a thin film such as sputtering or vapor deposition, a micro-contact printing method, or a nanoimprint method. In addition, the fine metal structures 30 can be formed by a colloid chemical method and the fine metal structures 30 may be disposed in a position separated from the metal layer 10 by a suitable method.

The fine metal structures 30 have a function of generating the localized surface plasmon in the electronic field enhancement element 100 of the embodiment. By irradiating the fine metal structures 30 with the excitation light, the localized surface plasmon (LSP) can be generated around the fine metal structures 30. The localized surface plasmon generated on the fine metal structures 30 and the propagating surface plasmon (PSP) generated on the metal layer 10 described above can perform the interaction in certain conditions.

1.3.1. Arrangement of Fine Metal Structures

The arrangement of the fine metal structures 30 is not particularly limited, as long as the fine metal structures 30 are disposed on the dielectric layer 20 and the propagating surface plasmon (PSP) can be excited on the metal layer 10 when the fine metal structures are irradiated with the incident light. The fine metal structures 30 may be arranged in a random manner, for example. Although the fine metal structures 30 are arranged in a random manner, if the fine metal structures are arranged in an island shape, the incident light from the sea part (part where the dielectric layer 20 is exposed) is incident to the dielectric layer 20, and accordingly, it is possible to generate the PSP in the vicinity of the boundary between the metal layer 10 and the dielectric layer 20. Therefore, the electromagnetic coupling between the LSP and the PSP occurs, and the effects which will be described later can be realized. However, there is a more preferable arrangement of the fine metal structures 30. Hereinafter, the preferable arrangement will be described.

In the embodiment, as shown in FIGS. 1 to 4, the plurality of fine metal structures 30 are aligned to configure metal columns 31. In the metal columns 31, the fine metal structures 30 are arranged in the first direction orthogonal to the thickness direction of the metal layer 10. That is, the metal columns 31 have a structure in which the plurality of fine metal structures 30 are aligned in the first direction orthogonal to the height direction. When the fine metal structures 30 have a shape having a longitudinal side (when the fine metal structures have an anisotropic shape), the first direction in which the fine metal structures 30 are aligned, may not coincide with the longitudinal direction thereof. The number of fine metal structures 30 aligned in one metal column 31 may be plural and is preferably equal to or greater than 10. The size (dimension), the shape, and the like of the fine metal structures 30 belonging to the metal column 31 may be the same or different from each other, as long as peak wavelengths of the localized plasmon generated on the fine metal structures 30 substantially coincide with each other.

Herein, a pitch of the fine metal structures 30 in the first direction in the metal column 31 is defined as a first pitch P1 (see FIGS. 2 and 4). The first pitch P1 indicates a distance between the centers of the gravity of two fine metal structures 30 in the first direction. When the fine metal structures 30 is a cylinder having the thickness direction of the metal layer 10 as a central axis, the distance between particles of the two fine metal structures 30 in the metal column 31 is equivalent to a length obtained by subtracting the diameter of the cylinder from the first pitch P1.

The pitch P1 of the fine metal structures 30 in the first direction in the metal column 31 is from 10 nm to 1 µm, preferably from 20 nm to 800 nm, more preferably equal to or greater than 30 nm and smaller than 780 nm, and even more preferably equal to or greater than 50 nm and smaller than 700 nm.

As an alignment method of the arrangement for aligning the plurality of fine metal structures in the first direction, the fine metal structures 30 may be aligned along the first direction, and the adjacent fine metal structures 30 may be deviated in the second direction to some extent, to have a staggered arrangement or a zigzag arrangement, as long as the metal column 31 can be specified. In the example shown in the drawings, the fine metal structures 30 in the metal column 31 are linearly aligned in the first direction.

The metal column 31 is configured with the plurality of fine metal structures 30 aligned in the first direction at the first pitch P1, and the distribution, the intensity, and the like of the localized surface plasmon generated on the fine metal structures 30 are also dependent on the arrangement of the fine metal structures 30. Accordingly, the localized surface plasmon interacting with the propagating surface plasmon generated on the metal layer 10 is not only the localized surface plasmon generated on the single fine metal structures 30, but may also include the localized surface plasmon by considering the arrangement of the fine metal structures 30 in the metal column 31.

As shown in FIGS. 1 to 4, the metal columns 31 are arranged to be aligned at a second pitch P2 in the second direction intersecting with the thickness direction of the metal layer 10 and the first direction. The number of aligned metal columns 31 may be plural and is preferably equal to or greater than 10.

Figure 5:
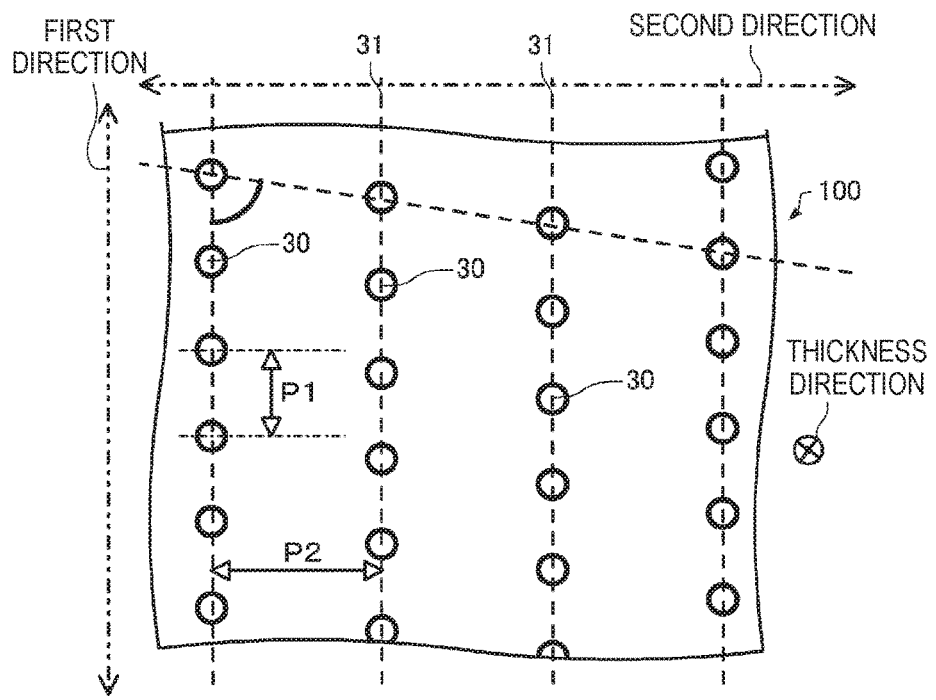
FIG. 5 is a schematic view when the electronic field enhancement element of the embodiment is seen in a thickness direction of a metal layer.
Figure 6:
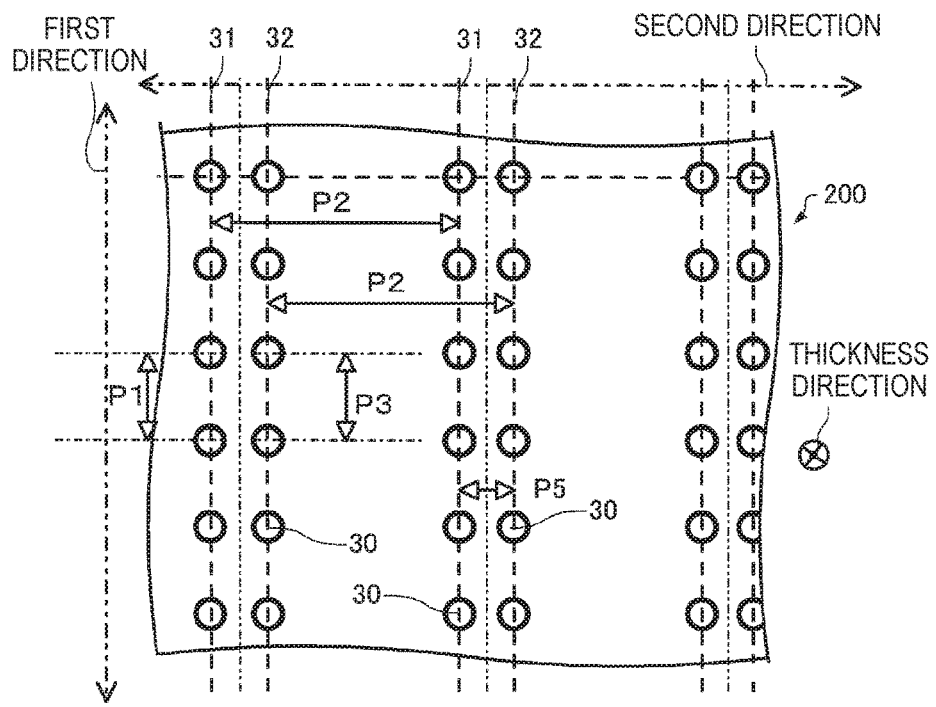
FIG. 6 is a planar schematic view showing an example of metal columns of the electronic field enhancement element.
Figure 7:
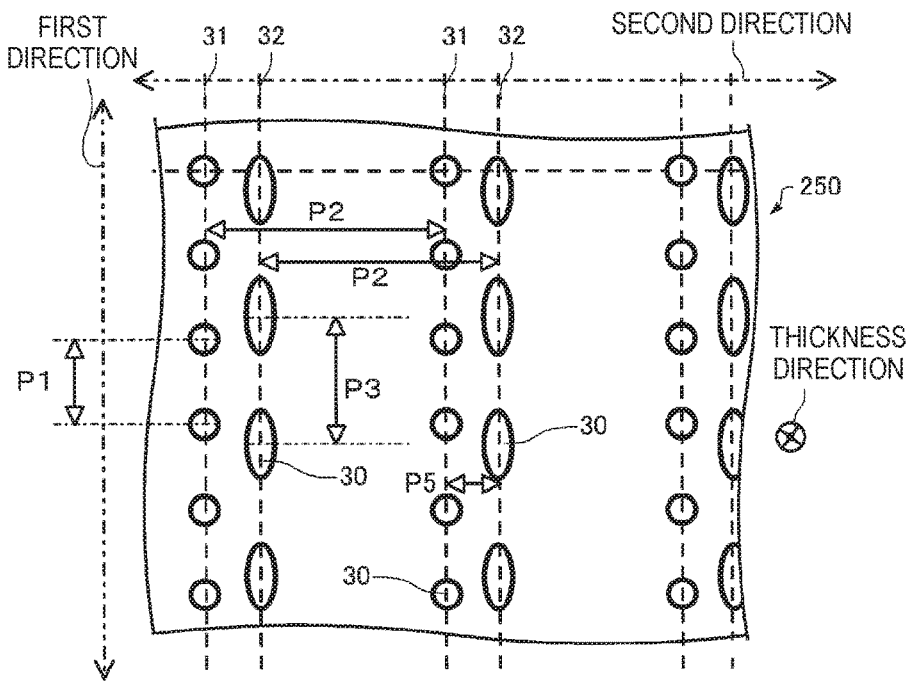
FIG. 7 is a planar schematic view showing an example of metal columns of the electronic field enhancement element.

Herein, a distance between the centers of the gravity of adjacent metal columns 31 in the second direction is defined as the second pitch P2 (see FIGS. 2, 5, 6, and 7: in the example shown in FIGS. 6 and 7, a set of the metal column 31 and the other metal column 32 is considered as one metal column, and a distance between the centers of gravity of the metal columns in the second direction is defined as the second pitch P2). The second pitch P2 between the metal columns 31 is set according to the conditions which will be described in the following "1.3.2. Propagating Plasmon and Localized Plasmon".

An angle formed by a line along the first direction in which the metal column 31 extends, and a line connecting the two fine metal structures 30 which respectively belong to the adjacent metal columns 31 and are closest to each other, is not particularly limited, and may be or may not be a right angle. For example, an angle formed by the two lines may be a right angle as shown in FIG. 2, or an angle formed by the two lines may not be a right angle as shown in FIG. 5. That is, when the arrangement of the fine metal structures 30 in the thickness direction is considered as a two-dimensional lattice in which the positions of the fine metal structures 30 are set as lattice points, an irreducible primitive unit lattice may have a rectangular shape or a shape of a parallelogram. When the angle formed by a line along the first direction in which the metal column 31 extends, and a line connecting the two fine metal structures 30 which respectively belong to the adjacent metal columns 31 and are closest to each other, is not a right angle, a pitch between the two fine metal structures 30 which respectively belong to the adjacent metal columns 31 and are closest to each other, may be set as the pitch P2.

In the electronic field enhancement element of the embodiment, as shown in FIGS. 6 and 7, the plurality of other metal columns 32 (metal column) in which the fine metal structures 30 are aligned in the first direction at a third pitch P3 may be further included. The other metal columns 32 are aligned in the second direction at the second pitch P2 and are arranged to be alternately aligned with the metal columns 31 in the second direction.

The other metal columns 32 may have the same configuration as that of the metal column 31 or may have a different configuration. The other metal columns 32 may be arranged to have one column for each metal column 31 or may be arranged to have plural columns for one metal column 31. A distance (pitch P5) between the other metal column 32 and the metal column 31 in the second direction can have a size of 1% to 50% of the pitch P2. The pitch P5 can be set independently of the pitch P1 of the fine metal structures 30 in the first direction.

When the plurality of the other metal columns 32 are arranged, these can be arranged to be separated at a distance having a size of 1% to 50% of the pitch P2 from each other in the second direction. When the other metal columns 32 have the same configuration as that of the metal columns 31 and are arranged in a position separated from the metal columns 31 at a distance of 50% of the pitch P2 in the second direction (when the pitch P5 is half of the pitch P2), this case is the same as a case where the metal columns 31 are arranged at a half pitch of the pitch P2, and accordingly, the other metal columns 32 arranged as described above are considered as the metal columns 31. When the other metal columns 32 are arranged in a position separated from the metal columns 31 at a distance of 50% or less of the pitch P2 in the second direction (when the pitch P5 is half or less than half of the pitch P2), a set of the other metal column 32 and the metal column 31 can be considered as one metal column (for example, the metal column 31).

At least one of the size (dimension), the shape, or the height of the position of the fine metal structures 30 belonging to the metal columns 31 and the fine metal structures 30 belonging to the other metal columns 32 may be the same as or different from each other, as long as the peak wavelengths of the localized plasmon generated on the fine metal structures 30 substantially coincide with each other.

FIGS. 6 and 7 are schematic views respectively showing an example of the other metal columns 32. FIG. 6 is a schematic view showing an example of an electronic field enhancement element 200 including the other metal columns 32 in which the plurality of fine metal structures 30 are aligned in the first direction at the third pitch P3 having the same size as that of the first pitch P1. FIG. 7 is a schematic view showing an example of an electronic field enhancement element 250 including the other metal columns 32 in which the plurality of fine metal structures 30 are aligned in the first direction at the third pitch P3 having a size different from that of the first pitch P1. As described above, the pitch P3 may be the same as or different from the pitch P1. When the plurality of the other metal columns 32 are provided, the pitch P3 of each column may be the same as or different from each other.

In the same manner as in the electronic field enhancement element 100, also in the electronic field enhancement element 200 and the electronic field enhancement element 250 according to the modification examples, the light can be enhanced in an extremely high enhancement degree based on the plasmon excited by the light irradiation. According to the analysis device including the electronic field enhancement element, it is possible to increase a degree of freedom when adjusting a profile of the enhancement degree of the electronic field enhancement element with respect to the wavelength of scattering light dependent on the material which is an analysis target. Therefore, it is possible to realize a sufficiently high plasmon enhancement effect with respect to wide analysis targets.

In the example shown in FIG. 6, the other metal columns 32 have the same configuration as that of the metal columns 31. That is, the fine metal structures 30 belonging to the other metal columns 32 have the same shape as that of the fine metal structures 30 belonging to the metal columns 31, and the pitch aligned in the first direction is the same for both metal columns (that is, pitch P1=pitch P3). In a case of this example, the fine metal structures 30 of the metal columns 31 and the fine metal structures 30 of the other metal columns 32 are arranged so as to be closest to each other (to be positioned in the first direction). However, the fine metal structures 30 belonging to the other metal columns 32 and the fine metal structures 30 belonging to the metal columns 31 may be arranged by deviation of the position of the fine metal structures 30 in the first direction.

When the metal columns 31 in which the fine metal structures 30 are aligned in the first direction at the pitch P1, and the other metal columns 32 in which the fine metal structures 30 are aligned in the first direction at the pitch P1 are arranged, it is possible to obtain the similar effect as in a case where the metal columns 31 are arranged in the second direction at the half pitch of the pitch P2. That is, in this case, the effect depends on the separated distance in the second direction between the metal columns 31 and the other metal columns 32, but it is possible to expect an effect that broadens the characteristics of the peak wavelength and causes hot spot density (HSD) to double, although the enhancement degree decreases, for example.

In the example shown in FIG. 7, the other metal columns 32 have different shapes and pitches from those of the metal columns 31. That is, the fine metal structures 30 belonging to the other metal column 32 have a shape different from that of the fine metal structures 30 belonging to the metal column 31, and the pitches aligned in the first direction are different each other between the pitch P1 of the metal column 31 and the pitch P3 of the other metal column 32 (that is, pitch P1<pitch P3).

The examples shown in FIGS. 6 and 7 merely show examples, and the other metal columns 32 can be suitably arranged by considering the excitation wavelength to be irradiated and the wavelength of Raman scattering light.

In the same manner as the first pitch P1, the second pitch P2 between the metal columns 31 is 10 nm to 2 µm, preferably 20 nm to 1500 nm, more preferably equal to or greater than 30 nm and smaller than 1000 nm, and even more preferably equal to or greater than 50 and smaller than 800 nm.

The first pitch P1 and the second pitch P2 may be the same (equivalent) as or different from each other. Herein, the expressions "same" and "equivalent" mean "same" and "equivalent" in terms of accepting a difference generated as a result of accumulation of manufacturing errors, or measuring errors. As one embodiment in which the first pitch P1 and the second pitch P2 are the same as each other, an embodiment in which the fine metal structures 30 are arranged in a two-dimensional square lattice shape (unit lattice is a square) where the fine metal structures 30 are arranged in the first direction at the first pitch P1, and arranged in the second direction orthogonal to the first direction at the second pitch P2 which is the same as the first pitch P1, is exemplified. As one embodiment in which the first pitch P1 and the second pitch P2 are the same as each other, an embodiment in which the fine metal structures 30 are arranged in a two-dimensional lattice shape (unit lattice is a rhombus) where the fine metal structures 30 are arranged in the first direction at the first pitch P1, and arranged in the second direction which is not orthogonal to but intersects with the first direction at the second pitch P2 which is the same as the first pitch P1, is exemplified.

An angle formed by a line along the first direction in which the metal column 31 extends, and a line connecting the two fine metal structures 30 which respectively belong to the adjacent metal columns 31 and are closest to each other, is not particularly limited, and may be or may not be a right angle. For example, an angle formed by the two lines may be a right angle or an angle formed by the two lines may not be a right angle. That is, when the arrangement of the fine metal structures 30 in the thickness direction is considered as a two-dimensional lattice in which the positions of the fine metal structures 30 are set as lattice points, an irreducible primitive unit lattice may have a rectangular shape or a shape of a parallelogram. When the angle formed by a line along the first direction in which the metal column 31 extends, and a line connecting the two fine metal structures 30 which respectively belong to the adjacent metal columns 31 and are closest to each other, is not a right angle, a pitch between the two fine metal structures 30 which respectively belong to the adjacent metal columns 31 and are closest to each other, may be set as the pitch P2.

1.3.2. Propagating Surface Plasmon and Localized Surface Plasmon

Figure 8:
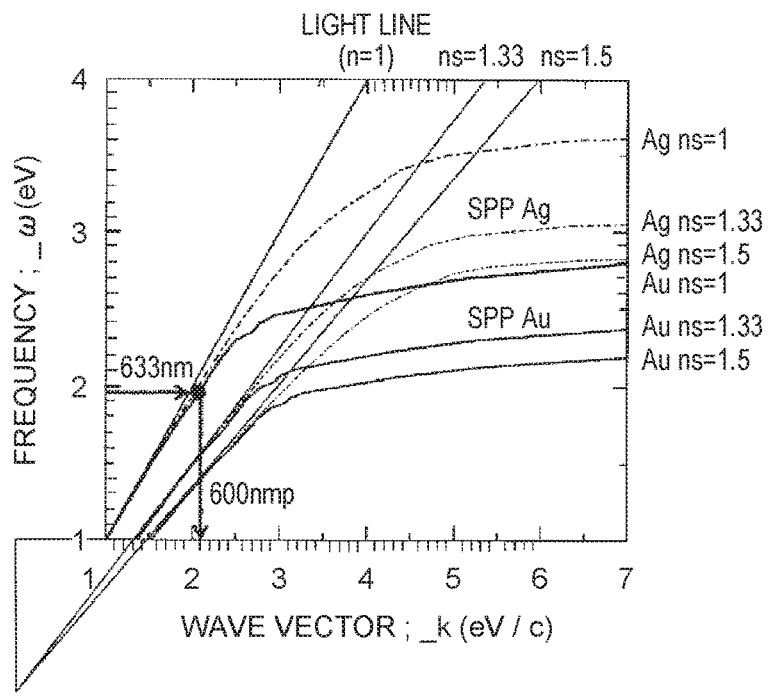
FIG. 8 is a graph of a dispersion relationship showing incident light and dispersion curves of gold and silver.

First, the propagating surface plasmon will be described. FIG. 8 is a graph of a dispersion relationship showing the excitation light and dispersion curves of gold (solid line) and silver (broken line). In general, the propagating surface plasmon is not generated even when the light is incident to the surface of the metal at an incidence light θ (irradiation angle θ) of 0 to 90 degrees. This is because, for example, when the metal is formed of Au, there is no intersection between a light line and a dispersion curve of SPP of Au, as shown in FIG. 8. In addition, even when the refractive index of a medium through which the light passes is changed, the SPP of Au also changes depending on the surrounding refractive index, and accordingly, no intersection is acquired. In order to make the intersection and generate the propagating surface plasmon, there is a method of providing the metal layer on the prism as Kretschmann configuration and increasing the wave number of the excitation light by the refractive index of the prism, or a method of increasing the wave number of the light line by diffraction grating. FIG. 8 is a graph showing a so-called dispersion relationship (the vertical axis indicates an angular frequency (ω(eV)) and the horizontal axis indicates a wave vector (k(eV/c))).

The angular frequency ω (eV) of the vertical axis of the graph of FIG. 8 satisfies a relationship of λ(nm)=1240/ω (eV) and can be converted into the wavelength. The wave vector k(eV/c) of the horizontal axis of the same graph satisfies a relationship of k(eV/c)=2π·2/(λ nm/100). Accordingly, when the diffraction grating interval is set as Q, for example, and Q=600 nm, k=2.09 (eV/c). In addition, the irradiation angle θ is an irradiation angle θ of the excitation light, and is an inclined angle in the thickness direction of the metal layer 10 or the dielectric layer 20 or the height direction of the fine metal structures 30.

FIG. 8 shows the dispersion curves of the SPP of gold (Au) and silver (Ag), but in general, when the angular frequency of the excitation light incident to the metal surface is set as w, the speed of light in vacuum is set as c, the dielectric constant of the metal configuring the metal layer 10 is set as ∈(ω), and the dielectric constant of the surrounding is set as ∈, the dispersion curve of SPP of the metal is applied with an expression (A) $K_{SPP}=\omega/c[\in\cdot\in(\omega)/(\in+\in(\omega))]^{1/2}$ ... (A).

Meanwhile, the irradiation angle of the excitation light which is the inclined angle in the thickness direction of the metal layer 10 or the dielectric layer 20 or the height direction of the fine metal structures 30 is set as θ, and the wave number K of the excitation light penetrating the diffraction grating having the interval Q can be expressed with an expression (B) $K=\in^{1/2}\cdot(\omega/c)\cdot\sin\theta+m\cdot 2\pi/Q$ ($m=\pm 1, \pm 2, \ldots$) ... (B). This relationship is expressed on the graph of the dispersion relationship as a linear line, not a curve.

In the graph of the dispersion relationship, when the dispersion curve of the SPP of the metal (expression (A)) and the linear line of the diffraction light (expression (B)) have an intersection, the propagating surface plasmon is excited. That is, when a relationship of $K_{SPP}=K$ is satisfied, the propagating surface plasmon is excited on the metal layer 10.

Accordingly, the following equation (2) is obtained from the expression (A) and the expression (B).

$$((\omega/c)\cdot\{\in\cdot\in(\omega)/(\in+\in(\omega))\})^{1/2}=\in^{1/2}\cdot(\omega/c)\sin\theta+2m\pi/Q(m=\pm 1,\pm 2,\ldots) \quad (2)$$

When a relationship of the equation (2) is satisfied, the excitation of the propagating surface plasmon on the metal layer 10 is understood. In this case, in a case of the example of the SPP of FIG. 8, the inclination and/or an intercept of the light line can be changed by changing θ and m, and the linear line of the light line can be intersected with the dispersion curve of the SPP of Au.

Next, the localized surface plasmon will be described. For the conditions for generating the localized surface plasmon on the fine metal structures 30, an expression (C) Real [∈(ω)]=−2∈ ... (C) by the real part of the dielectric constant is used. When the surrounding refractive index is set as 1, ∈=1, and therefore Real [∈(ω)]=−2.

Figure 9:
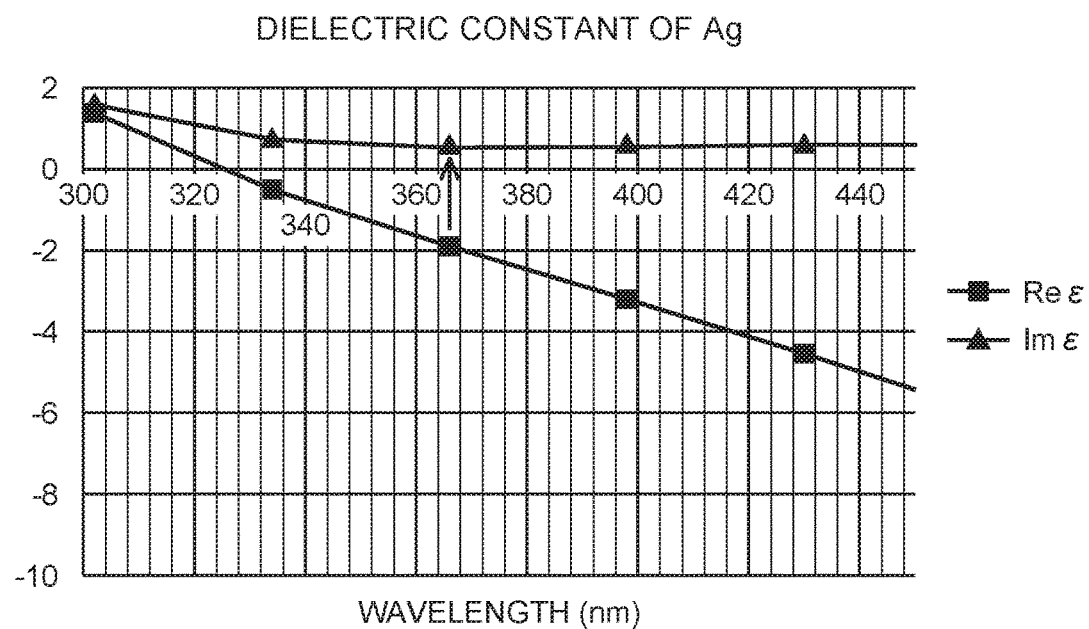
FIG. 9 is a graph showing a relationship between a dielectric constant and a wavelength of Ag.

FIG. 9 is a graph showing a relationship of the dielectric constant of Ag and the wavelength. For example, the dielectric constant of Ag is as shown in FIG. 9, and the localized surface plasmon is excited at a wavelength of approximately 366 nm, but in a case where a plurality of silver particles are closed in nano-order, or in a case where the silver particles and the metal layer 10 (Au film or the like) are disposed to be separated from each other by the dielectric layer 20, the excitation peak wavelength of the localized surface plasmon is subjected to red shift (long-wavelength side shift), when the refractive index n of the dielectric layer 20 increases. The amount of the shift is also dependent on dimensions of the diameter D of the silver particles, the thickness T of the silver particles, the particle interval of the silver particles, and the thickness G of the dielectric layer 20. In this case, the peak wavelength subjected to the red shift can be returned to the non-shifted wavelength (blue shift), by changing the diameter D of the silver particles, the thickness T of the silver particles, the particle interval of the silver particles, and the thickness G of the dielectric layer 20. With the investigation of the inventors, it is found that it is effective to decrease the diameter D of the silver particles among the diameter D of the silver particles, the thickness T of the silver particles, the particle interval of the silver particles, and the thickness G of the dielectric layer 20, as a parameter, for the blue shift.

The localized surface plasmon is plasmon which does not have the speed and does not move, unlike the propagating surface plasmon, and when the graph of the dispersion relationship is plotted, the inclination is zero, that is, ω/k=0.

Figure 10:
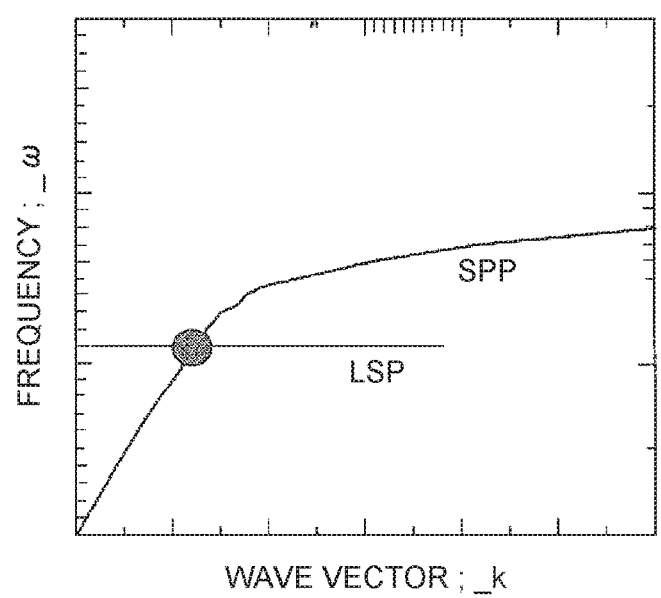
FIG. 10 is a graph showing a SPP dispersion relationship of gold and localized surface plasmon dispersion relationship.

FIG. 10 is a diagram showing the electromagnetic coupling of the dispersion relationships of the surface plasmon polariton (SPP) of the metal layer 10 and the localized surface plasmon (LSP) generated on the fine metal structures 30. In the electronic field enhancement element 100 of the embodiment, the enhancement degree having extremely great electronic field is obtained by electromagnetic coupling of the propagating surface plasmon and the localized surface plasmon. That is, in the graph of the dispersion relationship, as one of characteristics of the electronic field enhancement element 100 of the embodiment, the fine metal structures 30 which are the diffraction grating, are arranged so that the linear light of the diffraction light and the dispersion curve of the SPP of the metal do not intersect with each other at an arbitrary point, but intersects with each other in the vicinity of a point for applying greatest or maximum enhancement degree in the localized surface plasmon generated on the fine metal structures 30 (metal columns 31) (see FIG. 8). Accordingly, in the electronic field enhancement element 100 of the embodiment, the localized surface plasmon (LSP) excited on the fine metal structures 30 and the propagating surface plasmon (PSP) excited on the boundary of the metal layer 10 and the dielectric layer 20 electromagnetically interact with each other. When the electromagnetic coupling of the propagating surface plasmon and the localized surface plasmon is performed, an anticrossing behavior disclosed in OPTICS LETTERS/Vol. 0.34, No. 3/Feb. 1, 2009 occurs, for example.

That is, in the electronic field enhancement element 100 of the embodiment, since the graph of the dispersion relationship is designed so that the linear line of the diffraction light passes through the vicinity of the intersection of the dispersion curve of the SPP of the metal and the angular frequency (line parallel to the horizontal axis denoted as the LSP on the graph of the dispersion relationship in FIG. 10) of the excitation light applying the greatest or maximum enhancement degree in the localized surface plasmon generated on the fine metal structures 30 (metal columns 31), it is possible to realize an extremely high electronic field enhancement degree.

1.3.3. Second Pitch P2

As described above, the second pitch P2 between the metal columns 31 may be the same as or different from the first pitch P1. However, in a case where the excitation light is subjected to vertical incidence (angle of incidence θ=0) and the first-order diffraction light (m=0) is used, for example, it is possible to satisfy the equation (2) by employing the interval Q of the diffraction grating described above as the second pitch P2. However, the interval Q for satisfying the equation (2) with the selected angle of incidence θ and the order m of the diffraction light has a certain width. The angle of incidence θ in this case is preferably an inclined angle from the thickness direction towards the second direction, but may be an inclined angle towards a direction including a component of the first direction.

Accordingly, by considering the vicinity of the intersection described above (width of ±P1), the range of the second pitch P2 for generating the hybrid of the localized surface plasmon and the propagating surface plasmon may satisfy a relationship of an expression (D) Q−P1≤P2≤Q+P1 ... (D). The second pitch P2 may satisfy a relationship of P1≤P2 and may satisfy a relationship of the following expression (E).

$$P1 \leq P2 \leq Q + P1 \quad (E)$$

In general, in a case of the vertical incidence (the diffraction grating pitch passing through the intersection of the LSP and the SPP changes depending on the angle of incidence in a case of oblique incidence and this causes lack of description accuracy, and therefore, the case of the vertical incidence will be described), when the values of the first pitch P1 and the second pitch P2 are smaller than the wavelength of the excitation light, the intensity of the localized surface plasmon acting between the fine metal structures 30 tends to increase, and when the values of the first pitch P1 and the second pitch P2 are close to the wavelength of the excitation light, the intensity of the propagating surface plasmon generated on the metal layer 10 tends to increase. Since the electronic field enhancement degree of the entire electronic field enhancement element 100 also depends on the hot spot density (HSD; a rate of an area having high electronic field enhancement degree per unit area), the HSD decreases as the values of the first pitch P1 and the second pitch P2 increase. Accordingly, the values of the first pitch P1 and the second pitch P2 have the preferable range, and are preferable to satisfy the ranges of 60 nm≤P1≤1310 nm and 60 nm≤P2≤1310 nm, for example.

In a case where P1=P2, it is preferable that both P1 and P2 are approximately ±40% of the wavelength of the excitation light. Specifically, in a case where the wavelength of the excitation light is 633 nm, when both P1 and P2 are approximately 600 nm, the electronic field enhancement degree increases. In a case where the wavelength of the excitation light is 785 nm, when both P1 and P2 are approximately 780 nm, the electronic field enhancement degree increases.

Regarding the arrangement of the fine metal structures 30, it is preferable to satisfy a relationship of P1<P2, and the fine metal structures 30 may be arranged so as to satisfy a relationship of P1<P2≤Q+P1 ... (1). In this case, the arrangement of the fine metal structures 30 has anisotropy in a flat surface parallel to the dielectric layer 20. Accordingly, when the incident light is polarized light, the electronic field enhancement degree is different depending on a polarized component in the first direction and a polarized component in the second direction. In this specification, when the incident light is linearly polarized light in the first direction (linearly polarized light in a direction along the extension direction of the metal columns 31), the light is referred to as a "first line ⊥". When the incident light is linearly polarized light in the second direction (linearly polarized light in a direction intersecting the extension direction of the metal columns 31), the light is referred to as a "first line //".

When the fine metal structures 30 are arranged so as to satisfy the relationship of the expression (1), it is possible to obtain a high electronic field enhancement degree by irradiating the electronic field enhancement element 100 with the incident light of at least one kind of the linearly polarized light in the first direction, the linearly polarized light in the second direction, and circularly polarized light.

1.4. Surface Enhanced Raman Scattering

The electronic field enhancement element 100 of the embodiment shows a high electronic field enhancement degree. Accordingly, the electronic field enhancement element 100 can be suitably used in the measurement of the surface enhanced Raman scattering (SERS).

In the Raman scattering, when the wavelength of the excitation light is set as λi and the wavelength of the scattering light is set as λs, the shifted amount (cm$^{-1}$) due to the Raman scattering is obtained by the following equation (a).

$$\text{Shifted amount of Raman scattering}=(1/\lambda i)-(1/\lambda s) \quad (a)$$

Hereinafter, acetone will be described as an example of a target substance showing the Raman scattering effect.

It is known that the acetone causes the Raman scattering to occur with the shifted amounts of 787 cm$^{-1}$, 1708 cm$^{-1}$, and 2921 cm$^{-1}$.

With the equation (a), when the wavelength λi of the excitation light is set as 633 nm, the wavelengths λs of the stokes Raman scattering light due to the acetone are respectively, 666 nm, 709 nm, and 777 nm corresponding to the above-mentioned shifted amounts. In addition, when the wavelength λi of the excitation light is set as 785 nm, the wavelengths λs are respectively, 837 nm, 907 nm, and 1019 nm corresponding to the above-mentioned shifted amounts.

When detecting the acetone and determining the quantity of the acetone, it is not necessary to consider all of the peaks of the Raman scattering light, and it is only necessary to focus on the Raman scattering light on the shortest wavelength side, for example. The Raman shifted amount corresponding to the wavelength of the peak on the short wavelength side from the Raman scattering light of the acetone is 787 cm$^{-1}$, and if it is possible to perform the enhancement of the range corresponding to the shifted amount of approximately 0 cm$^{-1}$ to 1000 cm$^{-1}$ by the electronic field enhancement element 100, it is possible to detect the acetone and determine the quantity of the acetone with high sensitivity.

Although the acetone is used as an example herein, various kinds of the target substances have at least one Raman scattering peak in the range of the shifted amount of 0 cm$^{-1}$ to 1000 cm$^{-1}$. Accordingly, it is possible to detect various target substances and determine the quantity thereof with high sensitivity, by increasing the electronic field enhancement degree of the electronic field enhancement element 100 in a range of the wavelength corresponding to the shifted amount of 0 cm$^{-1}$ to 1000 cm$^{-1}$.

When the wavelength of the incident light is 633 nm, the range of the wavelength corresponding to the shifted amount of 0 cm$^{-1}$ to 1020 cm$^{-1}$ is from 633 nm to 677 nm, and when the wavelength of the incident light is 785 nm, the range of the wavelength is from 785 nm to 853 nm.

The anti-stokes scattering also occurs, but a probability of occurrence of the stokes scattering is high in principle, and in the SERS measurement, the stokes scattering in which the scattering wavelength is longer than the excitation wavelength is used in many cases, in general.

Meanwhile, in the SERS measurement, a phenomenon of dramatically increasing the intensity of the Raman scattering light having extremely low intensity using the electronic field enhancement effect by the surface plasmon is used. That is, a high electronic field enhancement degree Ei of the wavelength λi of the excitation light and a high electronic field enhancement degree Es of the wavelength λs of the Raman scattering light and the great HSD are required, and the SERS intensity is proportional to the following expression (b).

$$Ei^2 \cdot Es^2 \cdot HSD \quad (b)$$

However, Ei represents an electronic field enhancement degree at the wavelength λi of the excitation light, Es represents an electronic field enhancement degree at the wavelength λs of the Raman scattering light, and the HSD represents hot spot density and is the number of hot spots per certain unit area.

That is, in the measurement of the SERS, after grasping the wavelength of the excitation light to be used and the wavelength characteristics of the Raman scattering light of the target substance to be detected, the wavelength of the excitation light, the wavelength of the scattering light, and the wavelength of the peak of the electronic field enhancement degree (reflectance) spectrum of the surface plasmon are preferably designed to substantially coincide with each other, so that the SERS enhancement degree proportional to the expression (b) increases. An SERS sensor desirably has broadened peak of the electronic field enhancement degree (reflectance) spectrum and a value of the high enhancement degree.

When the surface plasmon resonance (SPR) is generated by the irradiation of the incident light (excitation light), the absorption due to the resonance occurs, and the reflectance decreases. Accordingly, the intensity of the SPR enhancement electronic field can be represented using the reflectance r (1−r). As the value of the reflectance r is close to zero, the intensity of the enhancement electronic field increases, and accordingly, it is possible to use the reflectance as an index of the intensity of the SPR enhancement electronic field. Therefore, in this specification, the enhancement degree profile (enhancement degree spectrum) and the reflectance profile (reflectance spectrum) are considered to be correlated to each other, and both of them are treated as the same components according to the above-mentioned relationship.

1.5. Enhancement Degree

A relationship of sizes between an electronic field Ex in an X direction (first direction) and an electronic field Ez in a Z direction (thickness direction), that is, a vector changes depending on a mesh position of the FDTD computation. In a case of using the linearly polarized light in the X direction as the excitation light, an electronic field Ey in a Y direction (second direction) can be substantially ignored. Accordingly, the enhancement degree can be grasped using the square-root of sum of squares of Ex and Ez, that is, SQRT $(EX^2+EZ^2)$. By doing so, the enhancement degrees can be compared with each other as scalar of local electronic field.

In the experimental examples or the drawings of this specification, the first direction may be referred to as the X direction, and this direction may be expressed as a symbol "X". In addition, the second direction may be referred to as the Y direction, and this direction may be expressed as a symbol "Y". The thickness direction of the element may be referred to as the Z direction, and this direction may be expressed as a symbol "Z".

As SERS enhancement factor (EF), the surface enhancement Raman scattering (SERS) effect is represented as an equation (c) SERS EF=Ei$^2$·Es$^2$·HSD . . . (c), by setting the electronic field enhancement degree at the wavelength of the excitation light as Ei and the electronic field enhancement degree at the wavelength after the Raman scattering as Es and using the hot spot density (HSD).

1.6. Incident Light

The wavelength of the incident light incident to the electronic field enhancement element 100 is not limited as long as it can generate the LSP and the PSP, and can be set as the electromagnetic wave containing ultraviolet light, visible light, and infrared light. In the embodiment, the incident light may be the linearly polarized light. The incident light may be linearly polarized light having an electronic field in the same direction as the first direction (extension direction of the metal columns 31) of the electronic field enhancement element 100, or may be linearly polarized light having an electronic field in the same direction as the second direction (aligning direction of the metal columns 31) of the electronic field enhancement element 100. In addition, the incident light may be the circularly polarized light. Further, it is possible to obtain an extremely great enhancement degree of the light by the electronic field enhancement element 100 by suitably combining the incident light beams having the different polarization direction.

The wavelength of the excitation light incident to the electronic field enhancement element 100 is not particularly limited, and can be set as the electromagnetic wave containing ultraviolet light, visible light, and infrared light. The excitation light can be, for example, at least one of the linearly polarized light which is polarized in the first direction, the linearly polarized light which is polarized in the second direction, and the circularly polarized light. By doing so, it is possible to obtain an extremely great enhancement degree of the light by the electronic field enhancement element 100.

When using the electronic field enhancement element 100 as the sensor of the SERS, it is possible to adjust the number, the size, and the shape (width) of the enhancement degree peak of the electronic enhancement spectrum with respect to the wavelength λi of the excitation light or the wavelength λs of the Raman scattering light of the target substance, in some cases, by substantially combining the linearly polarized light which is polarized in the first direction, the linearly polarized light which is polarized in the second direction, and the circularly polarized light as the excitation light.

1.7. Position of Hot Spot

When the electronic field enhancement element 100 of the embodiment is irradiated with the excitation light, an area having a great enhancement electronic field is generated at least on an end of the fine metal structure 30 on the upper surface side, that is, a corner of the fine metal structure 30 on the side far from the dielectric layer 20 (hereinafter, this position is referred to as "top" and a symbol "T" is noted in the drawing) and the end of the metal particle on the lower surface side, that is, a corner of the fine metal structure 30 on the side close to the dielectric layer 20 (hereinafter, this position is referred to as "bottom" and a symbol "B" is noted in the drawing). The corner of the fine metal structure 30 on the side far from the dielectric layer 20 corresponds to the apex of the fine metal structure 30, and indicates the vicinity of the perimeter of the (circular) surface on the side far from the dielectric layer 20, in a case where the fine metal structure 30 has a cylindrical shape having a normal direction of the dielectric layer 20 as a central axis, for example. In addition, the corner of the fine metal structure 30 on the side close to the dielectric layer 20 corresponds to the bottom of the fine metal structure 30, and indicates the vicinity of the perimeter of the (circular) surface on the side close to the dielectric layer 20, in a case where the fine metal structure 30 has a cylindrical shape having a normal direction of the dielectric layer 20 as a central axis, for example.

Since the fine metal structures 30 are arranged on the dielectric layer 20 to have a convex shape, it is considered that a probability of contact with the top of the fine metal structures 30 is greater than a probability of contact with the bottom thereof, when the target substance approaches the electronic field enhancement element 100. In addition, it is considered that the probability of contact with the bottom decreases, as the size of the target substance increases. In contrast, when the target substance is a substance having a small size, such as a gas molecule, it is considered that the probability of contact with the bottom relatively increases. In addition, depending on a manufacturing method of the fine metal structures 30, the cylindrical shape may not be obtained, but a saucer shape (a dome shape or a hemispherical shape) having the bottom larger than the top may be obtained. However, even in a case of such a shape, it is desirable to have a high enhancement degree of the bottom.

Meanwhile, in the electronic field enhancement element 100 of the embodiment, by changing the refractive index n of the dielectric layer 20, it is possible to change the energy for the electronic field enhancement of the electronic field enhancement element 100 by the energy distributed to the top and the energy distributed to the bottom. That is, when the refractive index n of the dielectric layer 20 is in a range of $1.46<n<2.5$, the maximum value of the enhancement degree of the electronic field enhancement element 100 is high and the electronic field enhancement degree of the bottom of the fine metal structure 30 is particularly high. Meanwhile, when the refractive index n of the dielectric layer 20 is in a range of $1\leq n<1.46$, although the maximum value of the enhancement degree of the electronic field enhancement element 100 decreases, the electronic field enhancement degree of the top of the fine metal structure 30 can be particularly increased.

Figure 11:
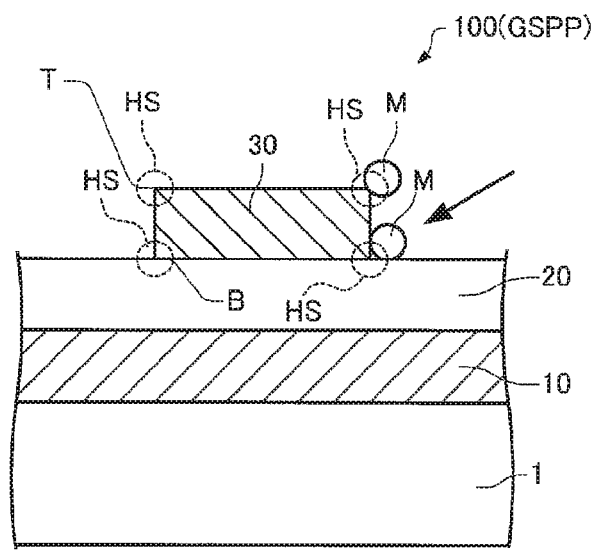
FIG. 11 is a schematic view showing main parts of the electronic field enhancement element of the embodiment.

FIG. 11 is a diagram schematically showing main parts of the electronic field enhancement element 100 of the embodiment (gap type surface plasmon polariton (GSPP)). As shown in FIG. 11, in the electronic field enhancement element 100 of the embodiment, the end portion of the fine metal structure 30 in a plan view which is the lower portion (bottom B) thereof on the dielectric layer 20 hardly comes in contact with an object M which is the measurement target. That is, in the GSPP model, the dielectric layer 20 exists in an area on the outer side of the outline of the fine metal structure 30 in a plan view and on the lower side of the fine metal structure 30 in a cross-sectional view. Accordingly, in the electronic field enhancement element 100 of the embodiment, when the object M (virus or compound) which is the measurement target approaches the fine metal structure 30, it is difficult to get near the bottom because the path for approaching the bottom B is narrow.

In contrast, as shown in FIG. 11, in the electronic field enhancement element 100 of the embodiment, the end portion of the fine metal structure 30 in a plan view which is the upper portion (top T) on the side opposite to the dielectric layer 20 easily comes in contact with the object M which is the measurement target.

The hot spot HS (area realizing a high electronic field enhancement degree) generated in the vicinity of one fine metal structure 30 is generated on the bottom B and the end portion of the fine metal structure 30 in a plan view which is the upper portion (top T) on the side separated from the substrate 1 (see FIG. 11). Regarding the bottom B and the top T, the distribution of the enhancement degree changes according to various conditions, and as described above, the intensity of the hot spot can be controlled by the refractive index n of the dielectric layer 20.

Accordingly, when the target substance is a substance having a comparatively small size so as to easily approach the bottom of the fine metal structure 30 (for example, a substance having a diameter equal to or smaller than 5 nm, for example), it is advantageous to realize the maximum value of the enhancement degree on the bottom B of the electronic field enhancement element 100 for the detection and the determination of the quantity. In contrast, when the target substance is a substance having a comparatively large size so as to hardly approach the bottom of the fine metal structure 30 (for example, a substance having a diameter greater than nm, for example), it is advantageous to increase the enhancement degree on the top T, even when the enhancement degree on the bottom B is low.

Therefore, when the target substance is a substance having a comparatively small size so as to easily approach the bottom of the fine metal structure 30, the refractive index n of the dielectric layer 20 is preferably in a range of $1.46<n<2.5$, and when the target substance is a substance having a comparatively large size so as to hardly approach the bottom of the fine metal structure 30, the refractive index is preferably in a range of $1\leq n<1.46$.

Thus, according to the electronic field enhancement element 100 of the embodiment, in addition to the small sample analysis of nano-order such as rare gas, it is possible to detect and determine the quantity with high sensitivity, even in a case of a measurement target substance having a large size which is equal to or greater than 5 nm such as the virus having a diameter of 20 nm to 100 nm or the like.

2. ANALYSIS DEVICE

Figure 12:
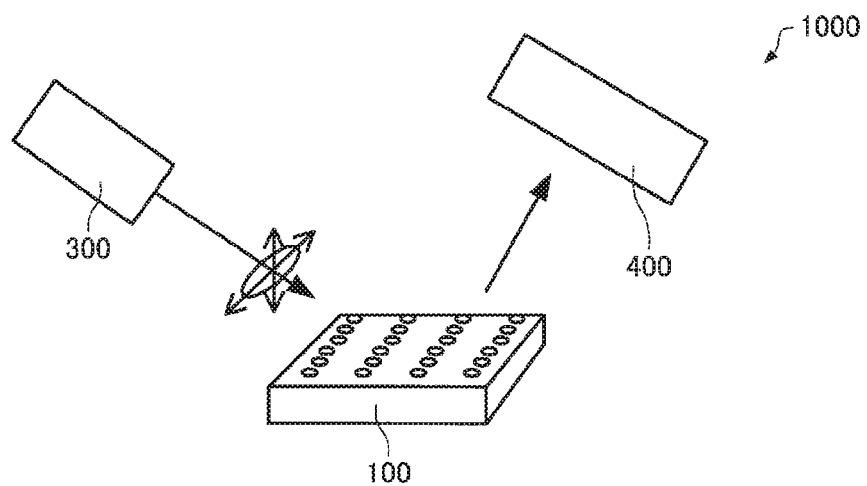
FIG. 12 is a schematic view of an analysis device of the embodiment.

FIG. 12 is a diagram schematically showing main parts of an analysis device 1000 of the embodiment.

The analysis device 1000 of the embodiment includes the electronic field enhancement element 100 described above, a light source 300 which irradiates the electronic field enhancement element 100 with the incident light, and a detector 400 which detects the light radiated from the electronic field enhancement element 100. The analysis device 1000 of the embodiment may have other suitable configurations not shown in the drawing.

2.1. Electronic Field Enhancement Element

The analysis device 1000 of the embodiment includes the electronic field enhancement element 100. The electronic field enhancement element 100 is the same as the electronic field enhancement element 100 described above, and therefore the specific description thereof will be described.

In the analysis device 1000, the electronic field enhancement element 100 performs an action of enhancing the light and/or an action as a sensor. The electronic field enhancement element 100 may be used to come in contact with the sample which is a target of analysis of the analysis device 1000. The disposition of the electronic field enhancement element 100 in the analysis device 1000 is not particularly limited, and the electronic field enhancement element may be installed on a stage, of which an installation angle can be adjusted.

2.2. Light Source

The analysis device 1000 of the embodiment includes the light source 300. The light source 300 irradiates the electronic field enhancement element 100 with the incident light. The light source 300 can emit the light (linearly polarized light in the same direction as the first direction) which is linearly polarized in the first direction of the electronic field enhancement element 100 (aligning direction of the fine metal structures 30 which is the extension direction of the metal columns 31), the light (linearly polarized light in the same direction as the second direction) which is linearly polarized in the second direction of the electronic field enhancement element 100 (aligning direction of the metal columns 31 which is the direction intersecting the extension direction of the metal columns 31), or the circularly polarized light.

That is, the light source 300 can irradiate the electronic field enhancement element 100 with the linearly polarized light in the same direction as the first direction and/or the linearly polarized light in the same direction as the second direction, or can irradiate the electronic field enhancement element 100 with the circularly polarized light. The inclined angle θ of the incident light emitted from the light source 300 in the thickness direction of the metal layer may be suitably changed depending on the excitation conditions of the surface plasmon of the electronic field enhancement element 100. The light source 300 may be installed in a goniometer or the like.

The light emitted by the light source 300 is not particularly limited as long as it can excite the surface plasmon of the electronic field enhancement element 100, and can be set as the electromagnetic wave containing ultraviolet light, visible light, and infrared light. The light emitted by the light source 300 may be or may not be coherent light. Specifically, as the light source 300, a component obtained by suitably providing a wavelength selection element, a filter, or a polarizer in a semiconductor laser, a gas laser, a halogen lamp, a high pressure mercury lamp, or a xenon lamp can be exemplified.

When the light source 300 includes the polarizer, the well-known polarizer can be used, and the polarizer may have a mechanism of suitably performing the rotation. The light from the light source 300 turns into the excitation light, the concentration of the electronic field due to the plasmon generated on the electronic field enhancement element 100, the so-called hot spot is generated, the weak Raman light of the substance attached to the hot spot is enhanced by the electronic field of the hot spot, and the detection of the substance can be performed.

2.3. Detector

The analysis device 1000 of the embodiment includes the detector 400. The detector 400 detects the light radiated from the electronic field enhancement element 100. As the detector 400, a charge coupled device (CCD), a photo multiplier, a photodiode, an imaging plate, or the like can be used, for example.

The detector 400 may be provided in a position for detecting the light radiated from the electronic field enhancement element 100, and the positional relationship between the detector and the light source 300 is not particularly limited. In addition, the detector 400 may be installed in a goniometer or the like.

3. ELECTRONIC APPARATUS

An electronic apparatus 2000 of the embodiment includes the analysis device 1000 described above, an operation unit 2010 which operates health care information based on the detected information from the detector 400, a storage unit 2020 which stores the health care information, and a display unit 2030 which displays the health care information.

Figure 13:
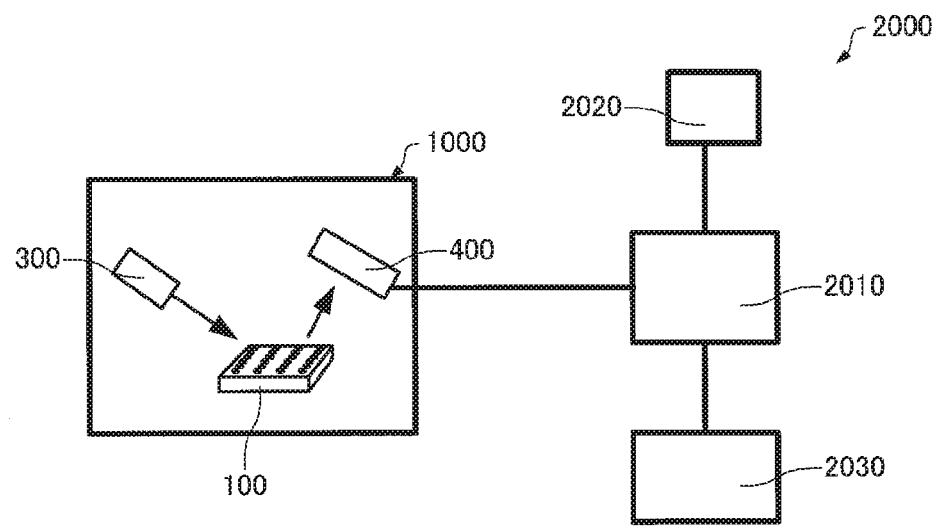
FIG. 13 is a schematic view of an electronic apparatus of the embodiment.

FIG. 13 is a schematic view of a configuration of the electronic apparatus 2000 of the embodiment. The analysis device 1000 is the analysis device 1000 described in "2. Analysis Device", and therefore the specific description thereof will be omitted.

The operation unit 2010 is, for example, a personal computer or a personal digital assistant (PDA), receives the detected information (signal or the like) transmitted from the detector 400 and performs the operation based thereon. The operation unit 2010 may control the analysis device 1000. For example, the operation unit 2010 may perform the control of the output and position of the light source 300 of the analysis device 1000 or the control of the position of the detector 400. The operation unit 2010 can operate the health care information based on the detected information from the detector 400. The health care information operated by the operation unit 2010 is stored in the storage unit 2020.

The storage unit 2020 is, for example, a semiconductor memory or a hard disk drive, and may be integrally configured with the operation unit 2010. The health care information stored in the storage unit 2020 is transmitted to the display unit 2030.

The display unit 2030 is configured with a display plate (liquid crystal monitor or the like), a printer, a luminous body, or a speaker, for example. The display unit 2030 displays or informs so that a user can check the content based on the health care information operated by the operation unit 2010.

The health care information can include information regarding at least one of biologically-relevant substances selected from a group consisting of bacteria, viruses, proteins, nucleic acid, and antigens and antibodies or existence or non-existence or an amount of at least one kind of compound selected from inorganic molecules and organic molecules.

4. EXPERIMENTAL EXAMPLES

Hereinafter, the invention will be further described by showing experimental examples, but the invention is not limited to the following examples. The following examples are simulations by a calculator. Each model was calculated using FDTD simulation. In addition, the incident light was subjected to vertical incidence and the linearly polarized light polarizing the electronic field in the X direction (first direction) was used. The background was set as a vacuum state or air space, and the refractive index of the background was calculated as $\in^{1/2}=1$.

Figure 14:
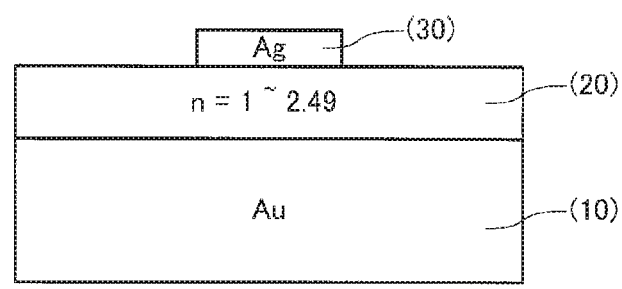
FIG. 14 is a schematic view showing an example of a model according to an experimental example.

In each experimental example, models schematically shown in FIG. 14 were used. A gold (Au) layer was used as a metal layer which was sufficiently thick so that the light does not penetrate therethrough, the material as the dielectric layer on the metal layer (Au) was not specified and the refractive index n thereof was changed in a range of 1 to 2.49. When n=1, air or a vacuum state is assumed, when n=1.46, $SiO_2$ is assumed, when n=1.64, $Al_2O_3$ of a thin film is assumed, when n=1.77, $Al_2O_3$ of bulk is assumed, when n=2.16, $Ta_2O_5$ is assumed, and when n=2.49, $TiO_2$ is assumed. As the fine metal structure on the dielectric layer, a cylindrical silver shape was set as a model of the gap type surface plasmon polariton (GSPP) formed in a certain period.

The material of the metal layer and the fine metal structure is not particularly limited. If the material is metal having a great negative real part of the dielectric constant and smaller imaginary part than the real part in the wavelength area of the excitation light, it can generate the plasmon.

Parameter Such as Calculation Model

In the graph shown in each experimental example, the notation of "X180Y600" is used, for example. "X180Y600" means that the fine metal structures 30 are arranged at the pitch of 180 nm (first pitch P1) in the first direction (X direction) and the pitch of 600 nm (second pitch P2) in the second direction (Y direction).

A case where the letter "D" and "T" are noted with numerical value indicates that the second metal layer used in the model has a cylindrical shape including a diameter D and a thickness T. A case where the letter "G" is noted with numerical value indicates a distance G (nm) between the metal layer 10 and the fine metal structures 30. Gap thickness in the horizontal axis of the graph indicates a distance G (nm) between the metal layer 10 and the fine metal structures 30. A case where the numerical value is noted from a range of "20 to 100", for example, shows that the numerical value is calculated using continuous or discrete value in the calculation of the above range.

"Ag" or "AG" in the drawing shows that the material of the focused configuration is silver, and "Au" or "AU" in the drawing shows that the material of the focused configuration is gold.

In addition, the notation is a symbol (abbreviation) for characterizing each model, and a case of the notation of X180Y600 model, for example, means that a second metal layer having a role of the diffraction grating is formed in a repetition period of the pitch of 180 nm in the X direction and a cycle period of the pitch of 600 nm in the Y direction. In contrast, X600Y180 model means that the second metal layer is formed in a repetition period of the pitch of 600 nm in the X direction and a repetition period of the pitch of 180 nm in the Y direction. Herein, the X600Y180 model also means that the incident light polarized in the Y direction (second direction) is incident, as in the case of the X180Y600 model.

In this specification, any of the X180Y600 model and the X600Y180 model is referred to as 1 line model. In addition, as a X180Y180 model, a model having small pitch in both the X direction and the Y direction is referred to as a basic model. When the linearly polarized light in the X direction is incident, a model having a small pitch in the polarization direction of the polarized light as the X180Y600 model, is referred to as 1 line ⊥ model, and a model having a small pitch in the direction orthogonal to the polarization direction of the polarized light as the X600Y180 model, is referred to as 1 line // model. A model having a great pitch in both X and Y directions and in which the PSP is strongly generated on a first metal layer (mirror layer) as the X600Y600 model, is referred to as a hybrid model.

A diameter of the fine metal structure of each model was set for each calculation so as to be a value for returning (blue shift) the red shift to the original wavelength.

Outline of Calculation

In the calculation, FDTD soft FullWAVE manufactured by Rsoft (current Cybernet Systems Co., Ltd.) was used. The condition of the used mesh was set as a minimum mesh of 1 nm and the calculation time cT was set as 10 μm.

Since the enhancement position (hot spot) satisfies with two components of electronic fields $E_x$ and $E_z$, all of the enhancement degrees of the following experimental example is represented by SQRT $(E_x^2+E_z^2)$. Herein, Ex shows the electronic field intensity in the polarization direction (first direction) of the incident light and Ez shows the electronic field intensity in the thickness direction. In this case, the electronic field intensity in the second direction is small and thus, is not considered. Hereinafter, SQRT $(E_x^2+E_z^2)$ may be simply referred to as "SQRT".

When the surface plasmon resonance (SPR) is generated by the irradiation of the excitation light, the absorption due to the resonance occurs and the reflectance decreases. Accordingly, the intensity of the SPR enhancement electronic field can be represented as (1−r) using the reflectance r. Since the intensity of the enhancement electronic filed is strong as the value of the reflectance r is close to zero, the reflectance may be used as an index of square of the intensity of the SPR enhancement electronic field (SQRT).

4.1. Experimental Example 1

Figure 15:
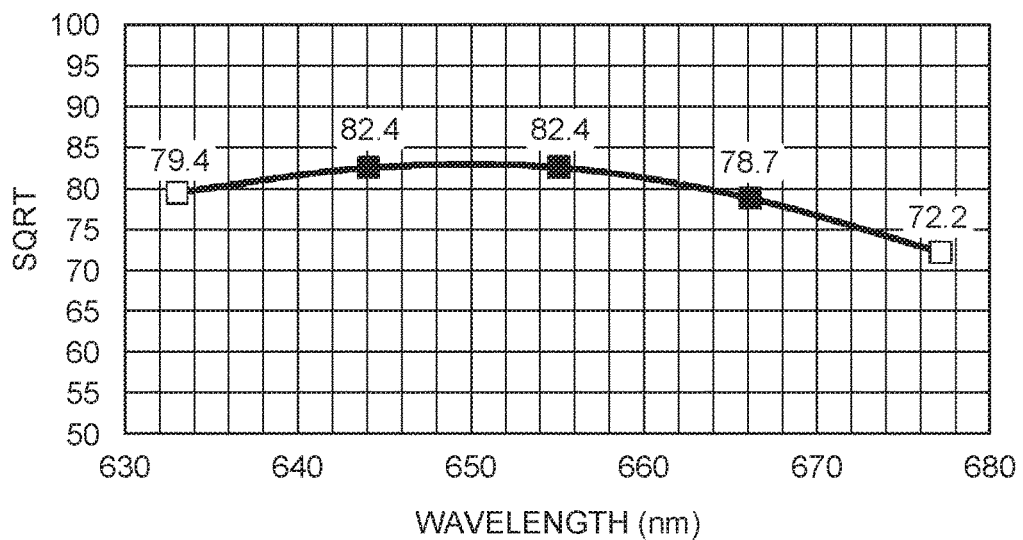
FIG. 15 is a graph showing wavelength dependence of SQRT regarding model X140Y140_64D30T_AU_20G_n=1.64 and model X140Y140_42D30T_AU_20G_n=2.16.
Figure 15:
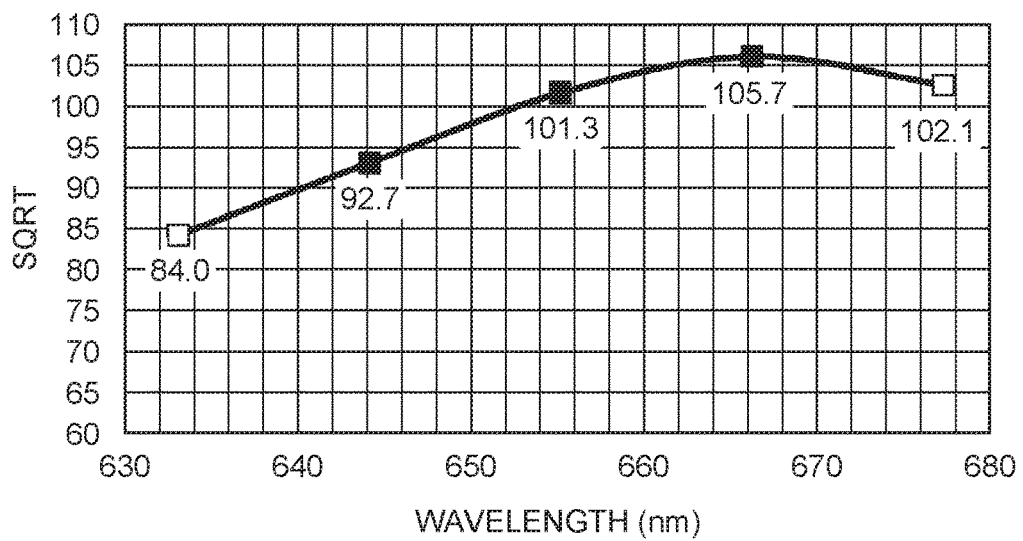

The Raman shifted amount at excitation of 633 nm was assumed to be equal to or smaller than 1020 $cm^{-1}$ (stokes Raman scattering wavelength of 677 nm). Accordingly, the conditions in which the SQRT becomes the peak at 655 nm which is the center wavelength between 633 nm and 677 nm. FIG. 15 is a graph showing wavelength dependence of SQRT regarding model X140Y140_64D30T_AU_20G_n=1.64 and model X140Y140_42D30T_AU_20G_n=2.16. From the result of FIG. 15, it could be checked that SQRT becomes the peak in the vicinity of 655 nm regarding the dimension of each model.

Figure 16:
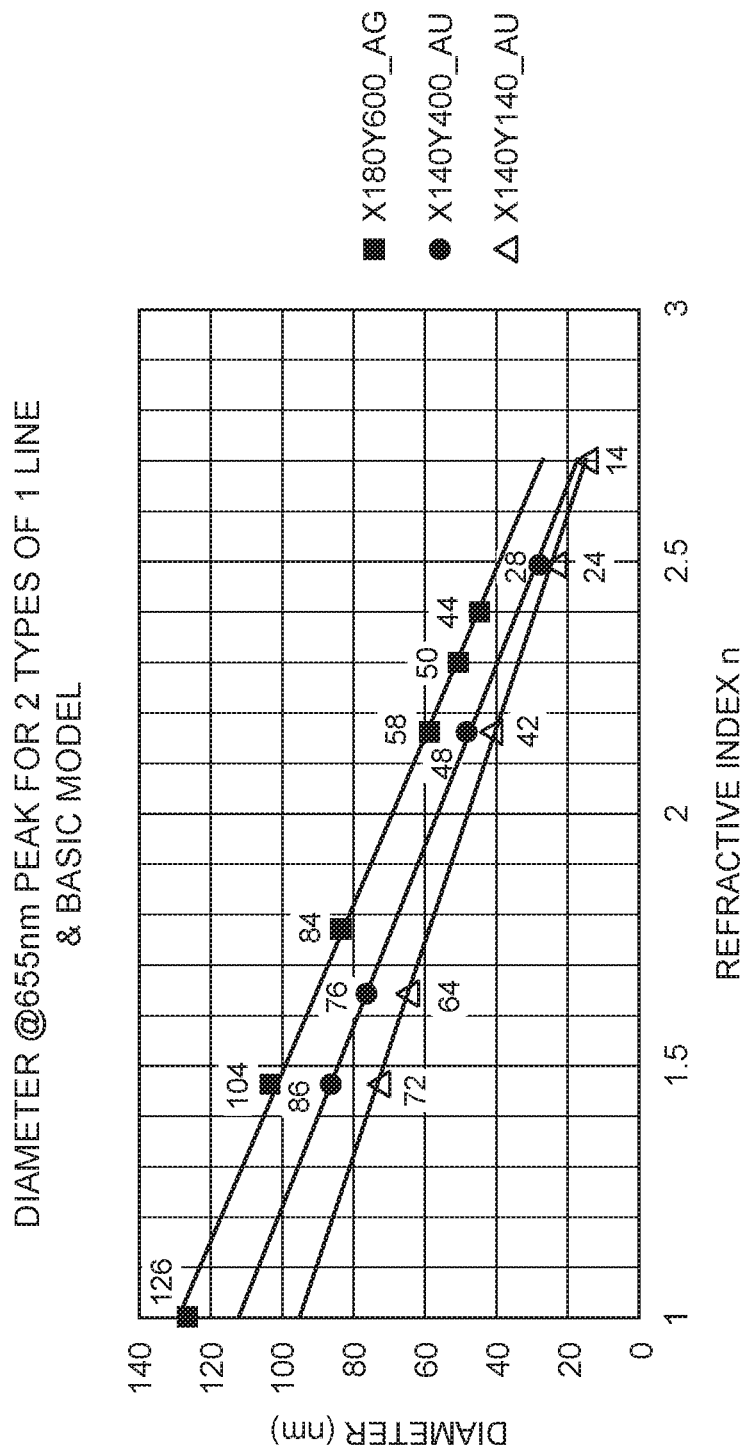
FIG. 16 is a graph in which a relationship between a diameter of a fine metal structure and a refractive index of a dielectric layer is plotted.

Next, a relationship of the diameter D of the fine metal structure and the refractive index n of the dielectric layer was investigated, regarding three types of models of X180Y600_AG model as 1 line model reference, and X140Y400_AU model and X140Y140_AU model in which the fine metal structure is assumed as gold and the density of the fine metal structures is increased by decreasing the length of the pitch in the Y direction. FIG. 16 is a graph in which the relationship between the diameter D of the fine metal structure and the refractive index n of the dielectric layer is plotted.

In FIG. 16, it was determined that the refractive index n of the dielectric layer and the diameter D of the fine metal structure are in a proportional relationship. That is, in any models, even when the refractive index n of the dielectric layer is increased and the peak of the enhancement degree profile is subjected to red shift, if the diameter D of the fine metal structure is decreased, it is possible to perform the blue shift of the peak, and it was determined that the enhancement degree can be increased with the shifted amount of 0 cm$^{-1}$ to 1020 cm$^{-1}$.

When the refractive index n of the dielectric layer is increased, it is found that the optimal value of the thickness G of the dielectric layer also changes, and the thickness G of the dielectric layer tends to be the optimal value on the side of the smaller refractive index. Accordingly, by considering two parameters of the diameter D of the fine metal structure and the thickness G of the dielectric layer, the conditions showing the peak value of SQRT (bottom of the fine metal structure) are searched at the excitation wavelength of 655 nm, and the collected results are shown in FIG. 17 (Table 1).

Figure 18:
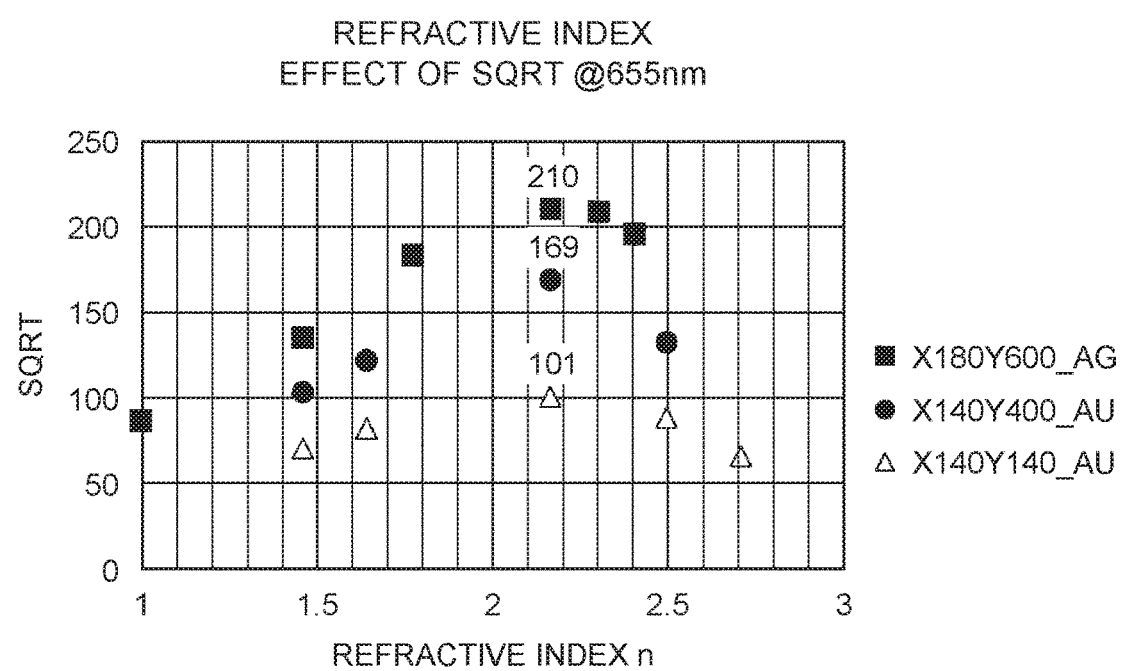
FIG. 18 is a graph showing refractive index dependence of SQRT of X180Y600_AG, X140Y400_AU, and X140Y140_AU.

FIG. 18 is a graph showing refractive index n of the dielectric layer dependence of SQRT of the three types of models of X180Y600_AG model, and X140Y400_AU model and X140Y140_AU model in which the fine metal structure is assumed as gold and the density of the fine metal structures is increased by decreasing the length of the pitch in the Y direction. The numerical values of each plot of the graph of FIG. 18 are noted in Table 1 described above. The plotting of the graph of FIG. 18 is performed by acquiring the thickness G of the dielectric layer and the diameter D of the fine metal structure to be the peak of the SQRT at the wavelength of 655 nm in all of the three types of models. In this case, the installation position of the monitor for calculation was XY (0,0,0.0005) (unit is μm), for setting the grid size of Yee-Cell as 1 nm and Straddle grid (a method of simulation of placing the face of Yee-Cell on the boundary surface of the material, therefore the calculation grid is shifted by 0.5 nm in the z direction) Yee-Cell setting in the XYZ directions.

By considering FIG. 18, when the refractive index n of the dielectric layer is greater than 1, the maximum value is obtained as n=2.16 regarding all of the three models, and the value decreases, when it becomes equal to or greater than that value.

Figure 19:
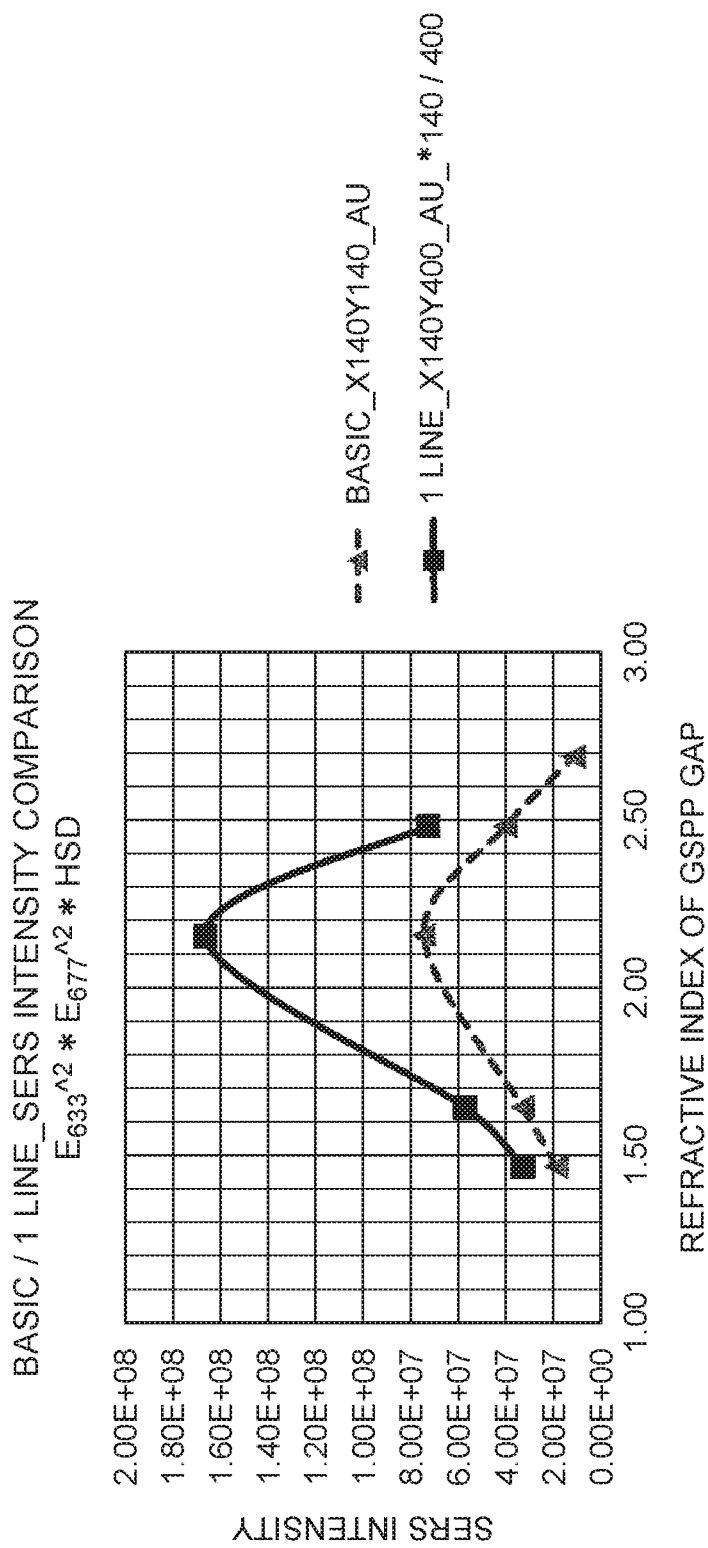
FIG. 19 is a graph showing a refractive index dependence of SERS intensity regarding model X140Y400_AU and model X140Y140_AU.

FIG. 19 is a graph showing dependence of a refractive index n of SERS intensity regarding the model X140Y400_AU and the model X140Y140_AU. The X140Y400_AU model is standardized by considering the HSD, and the value of the SERS intensity of both models can be directly compared to each other.

In FIG. 19, when the refractive index n of the dielectric layer of the standardized 1 line model (X140Y400_AU model) increases, the SERS intensity also increases, the maximum value which is extremely great as 1.6×10$^8$ is obtained, when n=2.16, and after that, the values decrease, but the large value of 7×10$^7$ is obtained, when n=2.49. Also in the basic model (X140Y140_AU model), when n=2.16, the action of obtaining the maximum value of the SERS intensity was the same. Herein, the maximum value of the SERS intensity was approximately 7×10$^7$ and was small compared to the 1 line model. It is considered that 1 line model shows the great contribution of the PSP generated on the metal layer.

4.2. Experimental Example 2

In the experimental example, a correlation between the value of the extinction coefficient κ and the value of SQRT was investigated. In general, regarding all of SiO$_2$, Al$_2$O$_3$, Ta$_2$O$_5$, and TiO$_2$, the extinction coefficient κ of the complex refractive index n' is zero. However, extinction coefficient κ of Si$_3$N$_4$ may be great as 0.016 (value in a case of the wavelength of 532 nm) or the extinction coefficient κ may not be zero depending on the manufacturing conditions of the thin film (film forming temperature, crystallinity, film forming method, partial pressure of gas, and the like).

Figure 20:
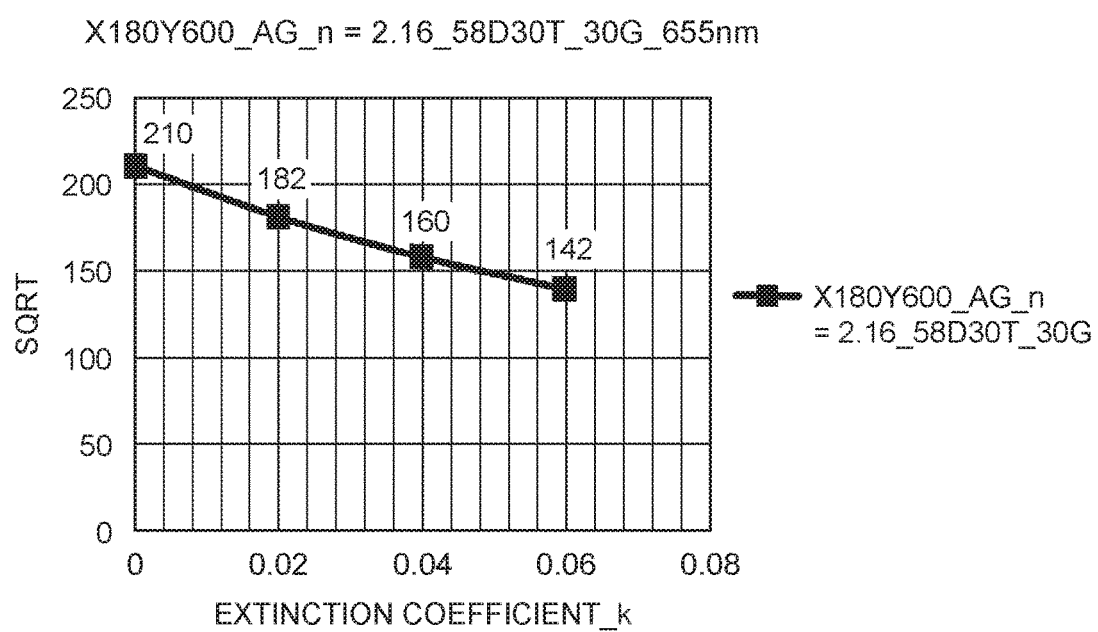
FIG. 20 is a graph showing an extinction coefficient dependence of model X180Y600_AG_58D30T_30G_n=2.16.

Therefore, the SQRT in a case where the extinction coefficient κ is set as 0, 0.02, 0.04, and 0.06 was acquired, regarding the model showing the highest SQRT, that is, the model of X180Y600_AG_58D30T_30G_n=2.16. The results thereof are shown in FIG. 20. Even when the extinction coefficient κ is not zero, the peak wavelength was 655 nm as in the case where κ=0.

When κ=0.06, SQRT=142, and this is substantially the same value as in the case where the dielectric layer is SiO$_2$. That is, the effect of increasing the refractive index n of the dielectric layer is great, but as a result of increasing the refractive index n, when the extinction coefficient κ is increased, it was found that the enhancement effect decreased. Accordingly, it was found that the selection and manufacturing methods of the material for setting the dielectric layer having a high refractive index and obtaining substantially zero extinction coefficient κ are important.

4.3. Experimental Example 3

In the experimental example, in the dependence of the refractive index n of the dielectric layer of SQRT, a reason for showing the action as in the experimental example 1 was investigated.

The value of the SQRT described above is a value of the bottom of the fine metal structure, and it was investigated which value of the hot spot of the bottom of the fine metal structure is shown.

Figure 21A:
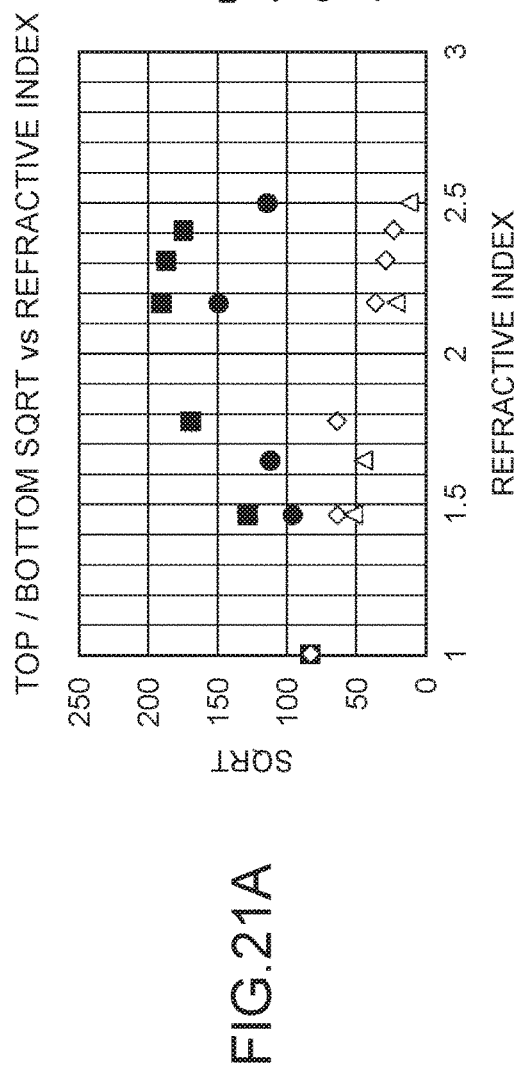
FIGS. 21A and 21B are graphs showing dependence of the refractive index of SQRT (FIG. 21A) in a position of the top and in a position of the bottom of the fine metal structures of models X180Y600_AG and X140Y400_AU, and a top/bottom ratio (FIG. 21B).
Figure 21B:
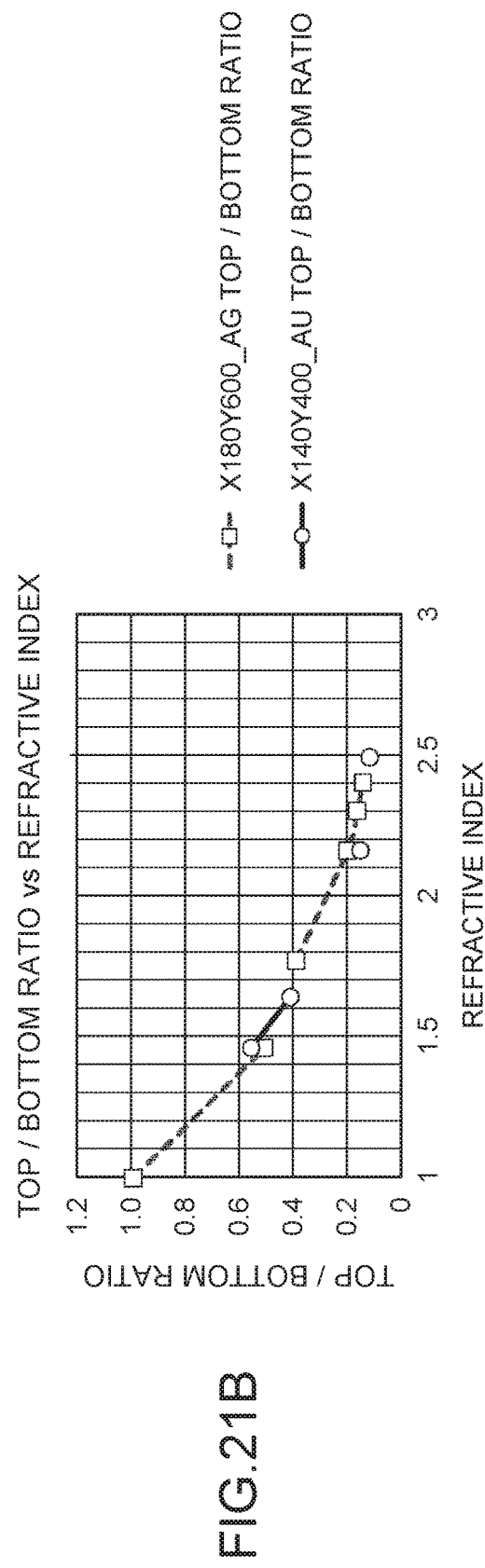

FIGS. 21A and 21B are a graph (a) showing dependence of the refractive index n of the dielectric layer of the SQRT of the position of the top and the position of the bottom of the fine metal structure, in the models of X180Y600_AG and X140Y400_AU, and a graph (b) showing dependence of the refractive index n of the dielectric layer of the ratio of top/bottom of the same models (SQRT of the top/SQRT of the bottom). In this case, the installation position of the monitor is XY (0,0,0) on the bottom and XY (0,0,0.03) on the top. The reason for the value of the SQRT of the bottom which is different from that of FIG. 18 of the experimental example 1 is because the monitor position is set as Z=0.5 nm in FIG. 18 and Z=0 nm in FIGS. 21A and 21B.

In FIGS. 21A and 21B, until n becomes 2.16 regarding both models, the enhancement degree of the bottom increases, as the refractive index n increases, but the enhancement degree of the top is highest when n=1, and it was found that the enhancement degree monotonously decreases, as the refractive index n increases.

That is, it is considered that the reason for the increased enhancement degree when the refractive index n of the dielectric layer increases, is that the positions of the hot spots concentrate to the bottom of the fine metal structures. In contrast, when the target substance is easily attached to the top of the fine metal structures, it was found that it is preferable to have the refractive index n of the dielectric layer approach to 1.

In FIG. 21B, in the 1 line ⊥ model (X180Y600_AG and X140Y400_AU models), it was determined that the ratios of top/bottom to the refractive index n are exactly the same as each other. Accordingly, it was found that the effect of the enhancement degree improvement due to the increase of the refractive index n of the dielectric layer does not depend on the pitch of the arrangement of the fine metal structure in the Y direction and the material (AU and AG) of the fine metal structures.

Meanwhile, in the dependence of the refractive index n of the dielectric layer of the SQRT, the reason for a decrease of the SQRT when the refractive index n increases, after the SQRT becomes the maximum value, was investigated.

A propagated distance $\delta_{SPP}$ of the SPP is represented by the following equation (X) and equation (Y).

$$\delta_{SPP}=1/[2 \cdot Im(k_{SPP})] \quad (X)$$

$$k_{SPP}=k'_{SPP}+ik''_{SPP}=(\omega/c)\cdot[\in_m\cdot\in_d/(\in_m+\in_d)]^{1/2} \quad (Y)$$

Herein, $k_{SPP}$ represents a complex wave number vector of the PSP in the direction parallel to the boundary of the metal layer and the dielectric layer, $Im(k_{SPP})$ represents the imaginary part of $k_{SPP}$, $k'_{SPP}$ and $k''_{SPP}$ respectively represent the real part and the imaginary part, $\omega$ represents the angular frequency, c represents the speed of light in vacuum, $\in_m$ and $\in_d$ respectively represent the complex dielectric functions of the metal layer and the dielectric layer.

Figure 22:
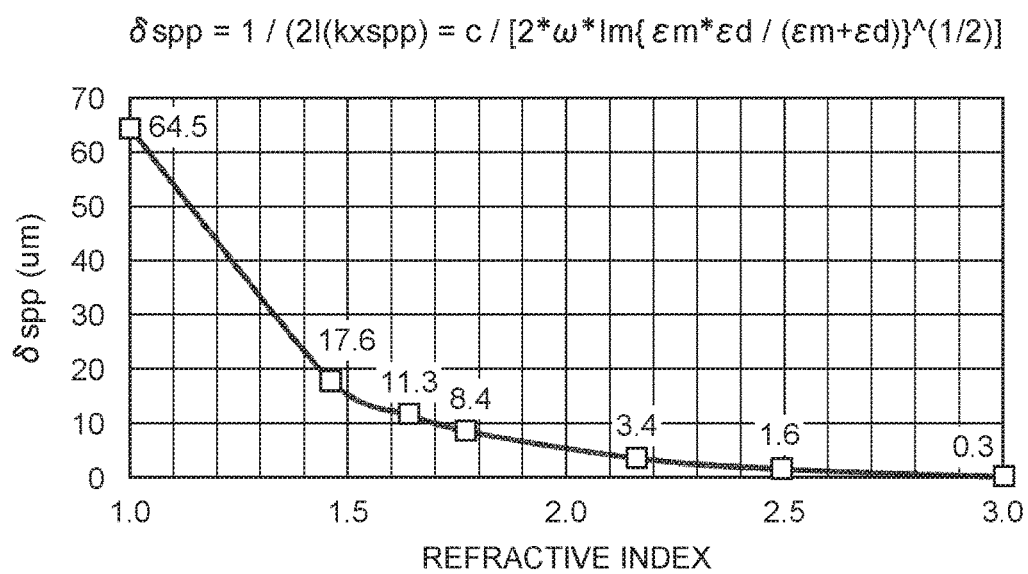
FIG. 22 is a graph showing dependence of the refractive index of the dielectric layer of the propagated distance of SPP.

When calculating the dependence of the refractive index n of the dielectric layer of the propagated distance $\delta_{SPP}$ of the SPP using the equation (X) and the equation (Y), the result is obtained as in FIG. 22.

As the propagated distance $\delta_{SPP}$ of the SPP is long, the SPP by the cycle structure becomes strong. In contrast, when the propagated distance $\delta_{SPP}$ of the SPP is short, attenuation of the SPP is strong, the interaction of the SPP generated by each grating is decreased, and as a result, the enhancement degree decreases.

In FIG. 22, when the circumferential refractive index is 2.16, the propagated distance of the SPP is 3.4 μm. Regarding the X180Y600 model, the 600 nm pitch in the Y direction is 0.6 μm, and regarding the X140Y400 model, the 400 nm pitch in the Y direction is 0.4 μm. When the propagated distances $\delta_{SPP}$ of the SPP when the refractive index is 2.16 are compared, it is sufficiently small as 3.4/0.6=5.6 to 3.4/0.4=8.5.

Meanwhile, when the circumferential refractive index is equal to or greater than 2.49, the propagated distances $\delta_{SPP}$ of the SPP is short as 1.6 μm and becomes 1.6/0.6=2.7 to 1.6/0.4=4 by comparing with the grating pitch, and the enhancement effect due to the SPP is decreased.

Herein, the propagated distances $\delta_{SPP}$ of the SPP of the boundary between the metal layer and the dielectric layer (infinite thickness) is shown. In a case of the GSPP manufacturing according to the invention, when the thickness G of the dielectric layer is equal to or smaller than 100 nm, the effect of the metal layer as a base cannot be ignored, and it is known that an effective refractive index $n_{eff}$ of the dielectric layer further increases compared to the refractive index of the general thin film. When $n_{eff}$=2.9 is substituted in the equation (X), $\delta_{SPP}$=0.483 μm.

From the above experimental examples, it was determined that the enhancement degree of the hot spot of the bottom B increases, by increasing the refractive index n of the dielectric layer in the GSPP_1 line model having high density of the fine metal structures. However, it is considered that, 2.16 of the refractive index n is set as the refractive index n for obtaining the maximum enhancement effect, if the refractive index exceeds that value, the propagated distance of the SPP is short, the interaction of the SPP by each gratings decreases, and the SQRT decreases.

Meanwhile, it was found that the enhancement degree of the top T increases as the refractive index n is close to 1. When the size of the target substance is small as nano-order (for example, equal to or smaller than 5 nm), the target substance may be absorbed to the bottom B, and the refractive index n of the dielectric layer is preferably close to 2.16, and when the size of the target substance is great to be equal to or greater than several nanometers (for example, equal to or greater than 10 nm), the target substance is hardly attached to the hot spot of the bottom B, and accordingly, it is preferable to increase the enhancement degree of the hot spot of the top T by causing the refractive index n of the dielectric layer to be close to 1.

The invention is not limited to the embodiments described above, and various modifications can be performed. For example, the invention includes the substantially the same configuration (for example, the configuration with the same function, method, and result, or the configuration with the same object and effect) as the configuration described in the embodiments. The invention includes the configuration obtained by replacing the unsubstantial part of the configuration described in the embodiments. The invention includes the configuration which realizes the same action effect as the configuration described in the embodiments or the configuration which can achieve the same object. The invention includes the configuration obtained by adding a well-known technology to the configuration described in the embodiments.

What is claimed is:

1. An analysis device comprising:
an electronic field enhancement element including a metal layer, a dielectric layer provided on the metal layer, and a plurality of fine metal structures provided on the dielectric layer;
a light source which irradiates the electronic field enhancement element; and
a detector which detects light radiated from the electronic field enhancement element,
wherein a refractive index n of the dielectric layer satisfies n'=n+iκ and is in a range of 1.46<n<2.5,
wherein a complex refractive index of the dielectric layer is n', an imaginary unit is i, and an extinction coefficient is κ,
wherein the fine metal structures are arranged at a first pitch P1 in a thickness direction of the dielectric layer and are arranged at a second pitch P2 in another direction intersecting with the thickness direction, and

P1<P2≤Q+P1, wherein Q represents a pitch of a diffraction grating in $((\omega/c)\cdot\{\in\cdot\in(\omega)/(\in+\in(\omega))\}1/2=\in1/2\cdot(\omega/c)\cdot\sin\theta+2m\pi/Q$ (m=±1, ±2, . . . )), and
an angular frequency of localized plasmon excited in the fine metal structures is ω, a dielectric constant of the metal configuring the metal layer is $\in(\omega)$, a circumferential dielectric constant of the metal layer is $\in$, the speed of light in vacuum is c, and an irradiation angle of the incident light which is an inclined angle in the thickness direction of the metal layer is θ.

2. The analysis device according to claim 1,
wherein the refractive index n of the dielectric layer is in a range of 1.8<n<2.2.

3. An electronic apparatus comprising:
the analysis device according to claim 2;
an operation unit configured to obtain health care information based on detected information from the detector;
a storage device configured to store the health care information; and a display configured to display the health care information.

4. The analysis device according to claim 1,
wherein the light source which irradiates the electronic field enhancement element with at least one of linearly polarized light in the first direction, linearly polarized light in the second direction, and circularly polarized light.

5. The analysis device according to claim 4,
wherein the detector detects Raman scattering light enhanced by the electronic field enhancement element.

6. An electronic apparatus comprising:
the analysis device according to claim 5;
an operation unit configured to obtain health care information based on detected information from the detector;
a storage device configured to store the health care information; and
a display configured to display the health care information.

7. An electronic apparatus comprising:
the analysis device according to claim 4;
an operation unit configured to obtain health care information based on detected information from the detector;
a storage device configured to store the health care information; and
a display configured to display the health care information.

8. An electronic apparatus comprising:
the analysis device according to claim 1;
an operation unit configured to obtain health care information based on detected information from the detector;
a storage device configured to store the health care information; and
a display configured to display the health care information.

9. An analysis device comprising:
an electronic field enhancement element including a metal layer, a dielectric layer provided on the metal layer, and a plurality of fine metal structures arranged on the dielectric layer at a first pitch P1 in a first direction and are arranged at a second pitch P2 in a second direction intersecting with the first direction;
a light source which irradiates the electronic field enhancement element; and
a detector which detects light radiated from the electronic field enhancement element,
wherein $P1 < P2 \leq Q + P1$, and
wherein Q represents a pitch of diffraction grating in $((\omega/c) \cdot \{\in \cdot \in(\omega)/(\in + \in(\omega))\}^{1/2} = \in^{1/2} \cdot (\omega/c) \cdot \sin\theta + 2m\pi/Q$ ($m = \pm 1, \pm 2, \ldots$)), and
an angular frequency of localized plasmon excited in the fine metal structures is $\omega$, a dielectric constant of the metal configuring the metal layer is $\in(\omega)$, a circumferential dielectric constant of the metal layer is $\in$, the speed of light in vacuum is c, and an irradiation angle of the incident light which is an inclined angle in the thickness direction of the metal layer is $\theta$, and
a refractive index n of the dielectric layer satisfies $n' = n + i\kappa$ and is in a range of $1 \leq n < 1.46$, wherein a complex refractive index of the dielectric layer is n', an imaginary unit is i, and an extinction coefficient is $\kappa$.

10. The analysis device according to claim 9,
wherein the light source which irradiates the electronic field enhancement element with at least one of linearly polarized light in the first direction, linearly polarized light in the second direction, and circularly polarized light.

11. The analysis device according to claim 10,
wherein the detector detects Raman scattering light enhanced by the electronic field enhancement element.

12. An electronic apparatus comprising:
the analysis device according to claim 11;
an operation unit configured to obtain health care information based on detected information from the detector;
a storage device configured to store the health care information; and
a display configured to display the health care information.

13. An electronic apparatus comprising:
the analysis device according to claim 10;
an operation unit configured to obtain health care information based on detected information from the detector;
a storage device configured to store the health care information; and
a display configured to display the health care information.

14. An electronic apparatus comprising:
the analysis device according to claim 9;
an operation unit configured to obtain health care information based on detected information from the detector;
a storage device configured to store the health care information; and
a display configured to display the health care information.

* * * * *